(12) United States Patent
Ecoff et al.

(10) Patent No.: US 9,039,876 B2
(45) Date of Patent: May 26, 2015

(54) TEST STRIP EJECTOR FOR MEDICAL DEVICE

(71) Applicant: Roche Diagnostics Operations, Inc., Indianapolis, IN (US)

(72) Inventors: Clint A. Ecoff, Indianapolis, IN (US); Bryan Rolfs, Chicago, IL (US); Anthony J. Uberta, III, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 378 days.

(21) Appl. No.: 13/673,422

(22) Filed: Nov. 9, 2012

(65) Prior Publication Data
US 2014/0001044 A1    Jan. 2, 2014

Related U.S. Application Data

(63) Continuation-in-part of application No. 13/538,023, filed on Jun. 29, 2012, now Pat. No. 8,715,571.

(51) Int. Cl.
*G01N 27/327* (2006.01)
*A61B 19/00* (2006.01)
*G01N 33/487* (2006.01)

(52) U.S. Cl.
CPC ............ *G01N 27/3273* (2013.01); *A61B 19/00* (2013.01); *G01N 33/4875* (2013.01)

(58) Field of Classification Search
CPC . G01N 27/3273; G01N 33/4875; A61B 19/00
USPC ..................... 204/403.01–403.15; 221/1, 258
See application file for complete search history.

(56) References Cited

U.S. PATENT DOCUMENTS

| | | | |
|---|---|---|---|
| 6,189,370 B1 | 2/2001 | Neel et al. | |
| 7,585,464 B2 | 9/2009 | Amano et al. | |
| 7,819,283 B2 | 10/2010 | Chambers et al. | |
| 8,057,753 B2 | 11/2011 | DeAngeli et al. | |
| 2005/0224345 A1 | 10/2005 | Taniike et al. | |
| 2007/0255114 A1 | 11/2007 | Ackermann et al. | |
| 2008/0229808 A1 | 9/2008 | Lee | |
| 2009/0108013 A1 | 4/2009 | Van der Velde et al. | |

(Continued)

FOREIGN PATENT DOCUMENTS

| | | |
|---|---|---|
| EP | 1321769 A1 | 6/2003 |
| EP | 1382968 A1 | 1/2004 |

(Continued)

*Primary Examiner* — J. Christopher Ball
(74) *Attorney, Agent, or Firm* — Harness, Dickey

(57) ABSTRACT

A test strip ejector system for receiving and ejecting a fluid testing medical device test strip includes a mechanism assembly supported by the device whereby user actuation of the mechanism assembly induces displacement of the test strip in at least a test strip ejection direction to eject the test strip. The mechanism assembly includes a power source and an electric motor such as a piezo-electric linear micro motor connected to the power source. The electric motor has an armature displaced when the electric motor is energized. A digital display/user interface is provided. Selection of an ejection function presented on the digital display/user interface initiates operation of the electric motor and displacement of the armature thereby displacing the test strip in the ejection direction. An operating system including a microprocessor is connected to the display/user interface. The microprocessor controls direction of operation and operating speed of the motor.

43 Claims, 23 Drawing Sheets

(56) References Cited

U.S. PATENT DOCUMENTS

| | | |
|---|---|---|
| 2009/0227854 A1 | 9/2009 | Ohama et al. |
| 2010/0012530 A1 | 1/2010 | Watanabe et al. |
| 2011/0040160 A1 | 2/2011 | Sakata et al. |
| 2011/0143562 A1 | 6/2011 | Wu et al. |
| 2011/0186588 A1 | 8/2011 | DeAngeli et al. |
| 2012/0143085 A1 | 6/2012 | Sauers et al. |

FOREIGN PATENT DOCUMENTS

| | | |
|---|---|---|
| EP | 1480037 A1 | 11/2004 |
| EP | 1983339 A1 | 10/2008 |
| EP | 1762848 B1 | 11/2008 |
| EP | 2071326 A1 | 6/2009 |
| JP | 2003114213 A | 4/2003 |
| JP | 2004101514 A | 4/2004 |
| WO | WO 02/08753 A2 | 1/2002 |
| WO | WO 2004/063747 A1 | 7/2004 |
| WO | WO 2005/080966 A1 | 9/2005 |
| WO | WO 2006/066123 | 6/2006 |
| WO | WO 2007/083773 A1 | 7/2007 |
| WO | WO 2008/016137 A1 | 2/2008 |
| WO | WO 2009/055643 A2 | 4/2009 |
| WO | WO 2010/139864 | 12/2010 |

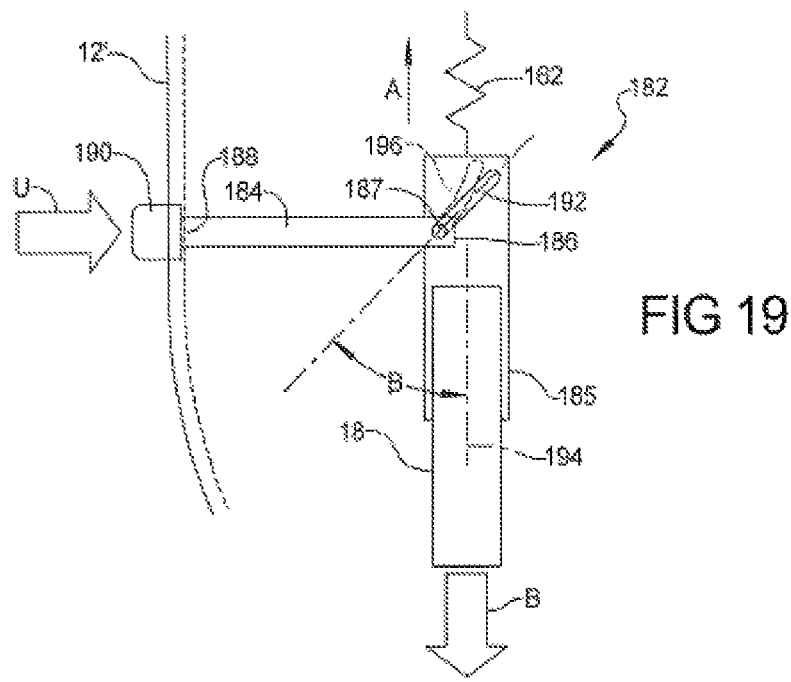
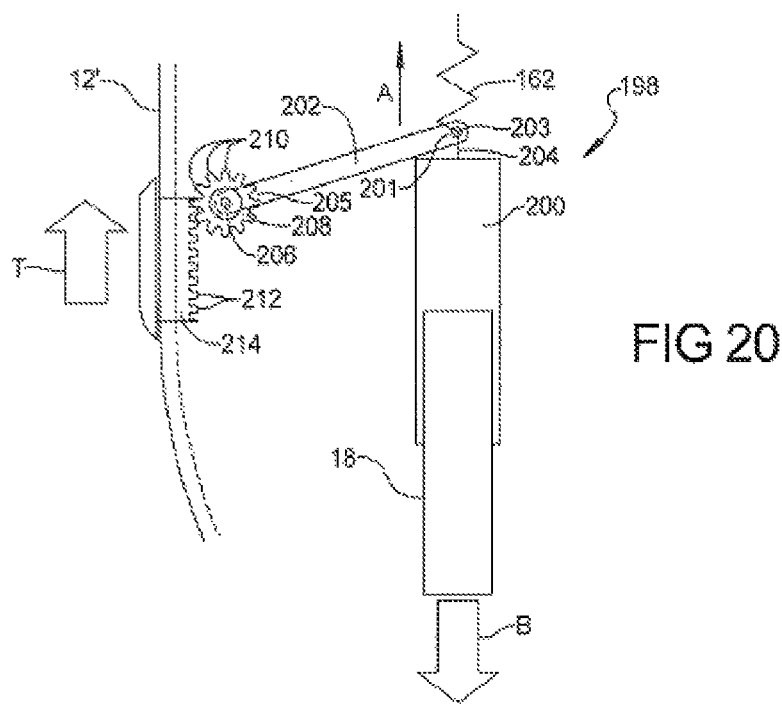

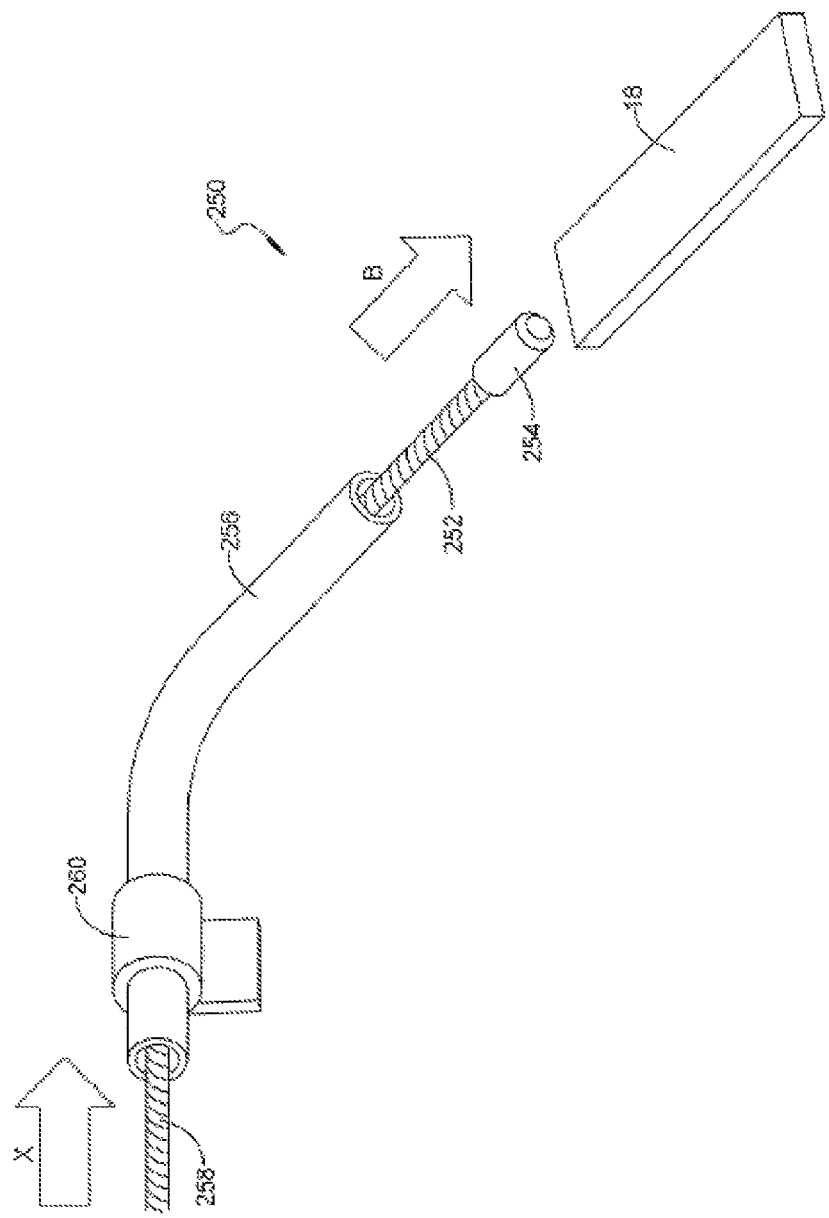

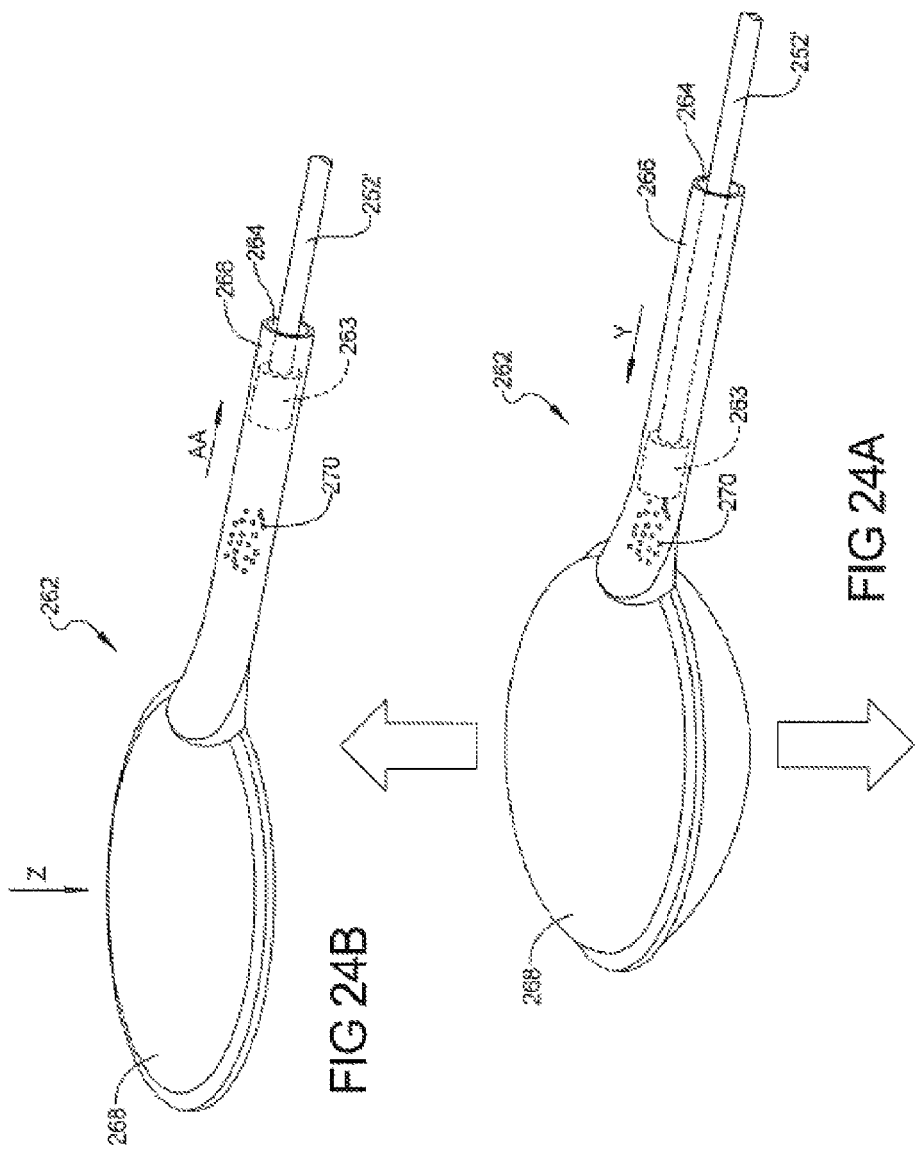

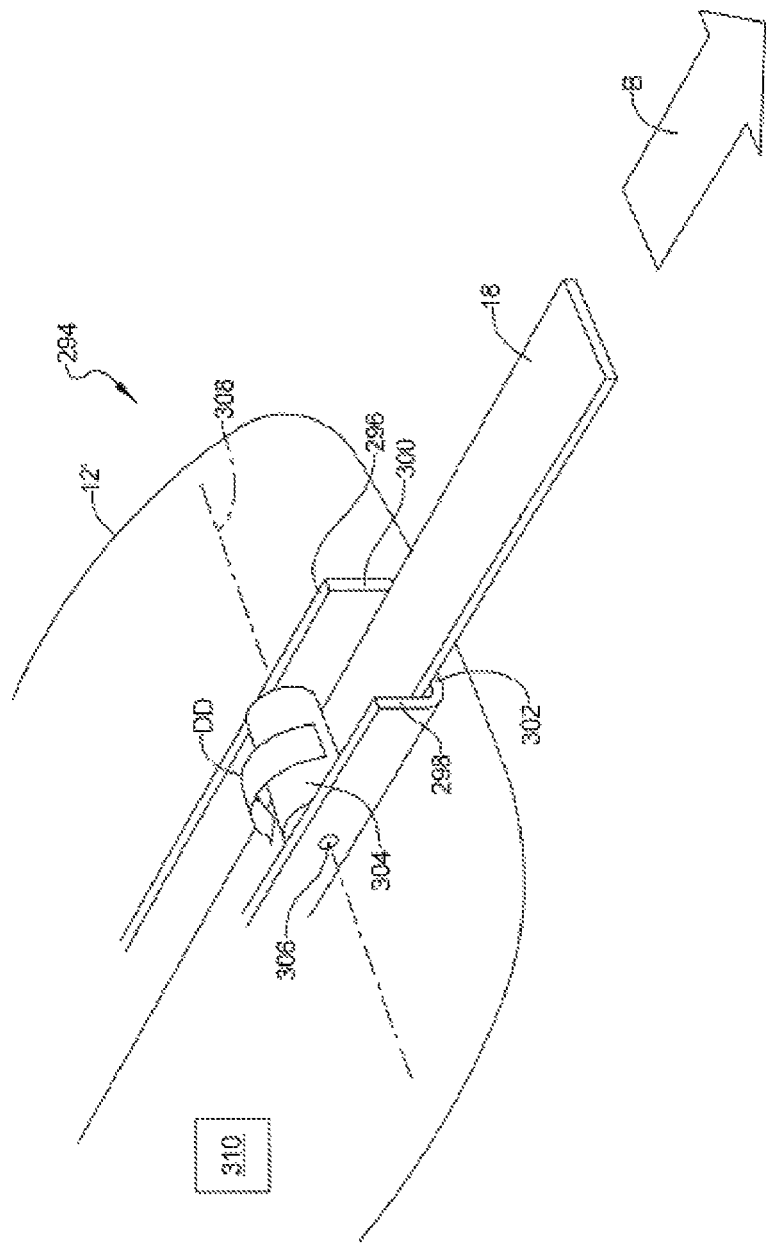

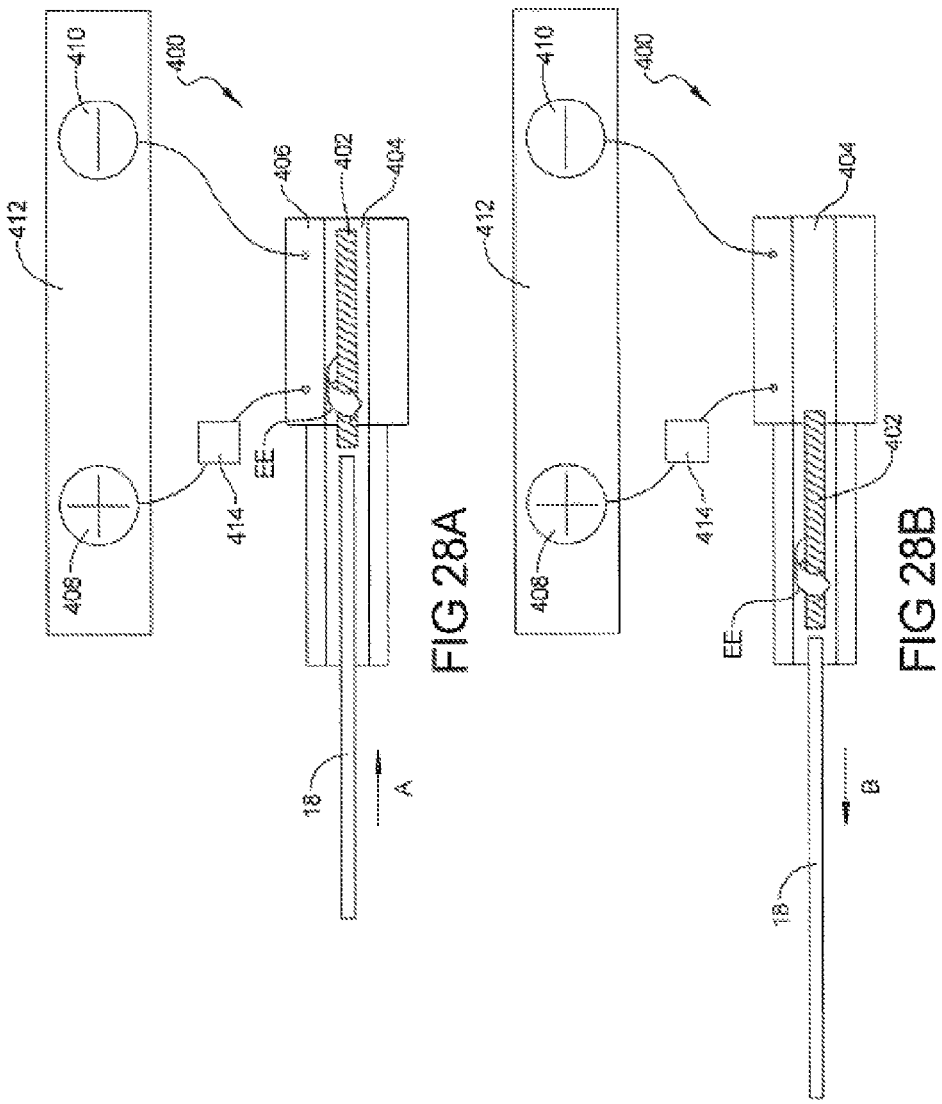

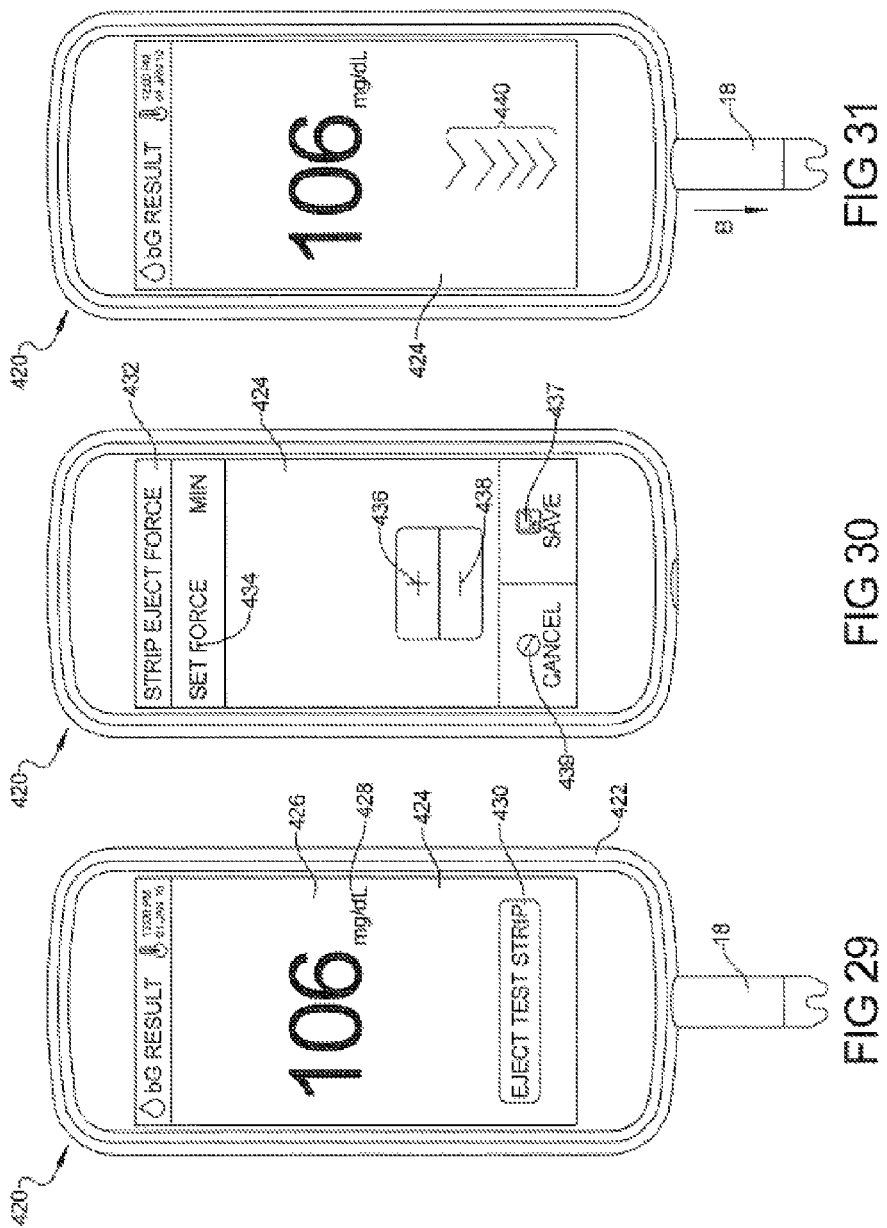

TEST STRIP EJECTOR FOR MEDICAL DEVICE

CROSS-REFERENCE TO RELATED APPLICATIONS

This application is a continuation-in-part of U.S. patent application Ser. No. 13/538,023 filed on Jun. 29, 2012. The entire disclosure of the above application is incorporated herein by reference.

FIELD

The present disclosure relates to a system and method for measuring a sample such as a body fluid, and more particularly to a device and method for loading and then ejecting a sample containing test strip following measurement.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides for readout of the glucose level.

Known meters receive the test strip in an insertion direction that also engages the electrical strip conductors of the test strip with the electrical contacts of the meter. As the test strip is loaded by the user, the insertion motion is used to drive the electrical contacts of the test strip into engagement with the contacts of the meter. The strip ejection system permits ejection of the dosed test strip following testing without further contact of the test strip by the user. Any interference with or sliding contact of the electrical contacts of the test strip during insertion, however, can damage the electrical contacts or misalign one or more of the contacts. A force applied to eject the test strip of known strip ejection systems can also cause racking or rotation of the test strip which can bind the test strip or interfere with ejection.

For example, the measurement device of U.S. Published Patent Application No. 2010/0012530 to Watanabe et al. includes a pushing member 11 having projection part 11b that is slidably guided within a pushing member cover 12. Clearance between the projection part 11b and pushing member 12 therefore limits the control available to reduce deflection of pushing member 11 during its travel to displace a sensor 200. In addition, pushing member 11 includes a single substantially centrally positioned projection part 11a guided in a notch 10a. Control of racking of the pushing member 11 during travel is limited by the tolerances between the projection part 11b and pushing member cover 12, and between the projection part 11a and notch 10a. A braking system having a first braking part 13 in contact with a side wall of the sensor 200 is provided to slow down the exit speed of the sensor. This system does not preclude racking of either the pushing member 11 or the sensor 200, has only the single projection part 11b to contact and drive the sensor 200 which can therefore be off-center of the sensor 200, and adds the complexity of a braking system to limit ejection velocity.

European Patent Application EP 1321769 to Pugh appears to disclose a test strip dispensing system having strip push members 116, 210 guided between rails 100 or 214. Rails of this design are positioned external to the strip push members. The strip push members include outer wall areas such as ledges 220 acting as guides. Ledges 220, however, are positioned within the rails 214, therefore continuous positive contact between the strip push members 116, 210 and the rails to limit racking is not provided and racking can occur due to a tolerance between the components. The design of strip push members 116, 210 and rails 100, 214 also precludes installation in a direction perpendicular to the push member travel direction.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one embodiment of the disclosure, a test strip ejector system for receiving and ejecting a test strip of a fluid testing medical device includes a mechanism assembly supported by the fluid testing medical device. User actuation of the mechanism assembly induces displacement of the test strip in at least a test strip ejection direction to eject the test strip. The mechanism assembly includes a power source and an electric motor connected to the power source. The electric motor has an armature displaced when the electric motor is energized. A digital display/user interface is provided. Selection of an ejection function presented on the digital display/user interface initiates operation of the electric motor and displacement of the armature thereby displacing the test strip in the ejection direction.

In another embodiment, a test strip ejector system for receiving and ejecting a test strip of a fluid testing medical device includes a mechanism assembly supported by the fluid testing medical device whereby user actuation of the mechanism assembly induces displacement of the test strip in at least a test strip ejection direction to eject the test strip. The mechanism assembly includes a power source and an electric motor connected to the power source. The electric motor has an armature displaced when the electric motor is energized. A digital display/user interface is provided. Selection of an ejection function presented on the digital display/user interface initiates operation of the electric motor and displacement of the armature thereby displacing the test strip in the ejection direction. An operating system including a microprocessor is connected to the display/user interface. The microprocessor controls direction of operation and operating speed of the motor.

In another embodiment, the electric motor is a piezo-electric linear micro motor having an armature displaced when the motor is energized, the armature directly contacting and ejecting the test strip.

In a further embodiment, an operating system includes a microprocessor connected to the power source and the motor and an accelerometer. The microprocessor controls direction of operation and operating speed of the motor. The accelerometer acts when an orientation of the fluid testing medical device is changed to initiate operation of the motor.

In a further embodiment, a test strip ejector system for receiving and ejecting a test strip of a fluid testing medical device includes a test strip slidably received in a receiving slot of the fluid testing medical device in a test strip loading direction. A mechanism assembly is supported by the fluid testing medical device whereby user actuation of the mechanism assembly induces displacement of the test strip in a test strip ejection direction opposite to the loading direction to eject the test strip. The mechanism assembly includes a power source; and an electric motor connected to the power source. The electric motor has an armature displaced when the electric motor is energized. A digital display/user interface is provided. Selection of an ejection function presented on the digital display/user interface initiates operation of the electric motor and displacement of the armature thereby displacing the test strip in the ejection direction.

In a further embodiment, a method is provided for receiving and ejecting a test strip by a mechanism assembly of a fluid testing medical device. The mechanism assembly includes a power source, an electric motor having an armature, a digital display/user interface and an operating system. The method includes: supporting the mechanism assembly by the fluid testing medical device; connecting the electric motor to the power source; manually inserting a test strip into the fluid testing medical device; and selecting an ejection function presented on the digital display/user interface to initiate operation of the electric motor and displacement of the armature thereby displacing the test strip in an ejection direction.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 19 shows a top plan view of another aspect for a push-button actuated test strip ejection mechanism;

FIG. 20 shows a top plan view of another aspect for a gear and arm test strip ejection mechanism;

FIG. 23 shows a front perspective view of another aspect for a cable and piston actuated test strip ejection mechanism;

FIGS. 24A and 24B show front perspective views of another aspect for a fluid bladder actuated test strip ejection mechanism;

FIG. 26 shows a front right perspective view of another aspect for a roller displacement test strip ejection mechanism;

FIGS. 28A and 28B show partial cross sectional front elevational views of another aspect for an electric motor actuated test strip ejection mechanism;

FIG. 29 shows a top plan view of an analysis device having a push button screen for automatic test strip ejection;

FIG. 30 shows a top plan view of the analysis device of FIG. 29 push button screen for selection of test strip ejection force;

FIG. 31 shows a top plan view of the analysis device of FIG. 29 push button screen for manual selection of test strip ejection velocity.

Figure 1:
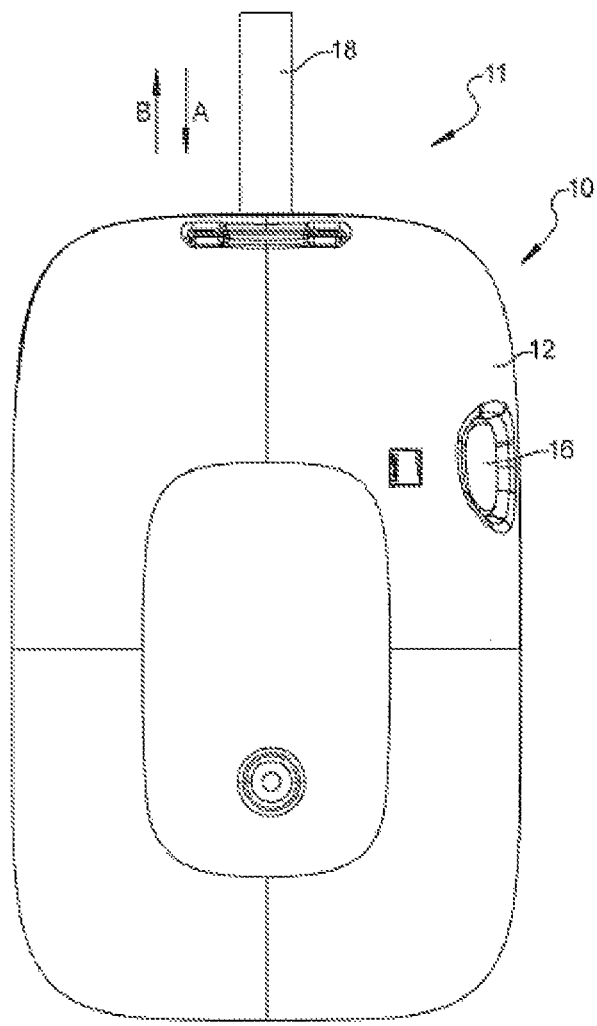
FIG. 1 shows a rear plan view of a fluid analysis device having a test strip ejector of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Referring now to FIG. 1, an analysis device 10 of a test strip ejector system 11, which can be used for example for testing blood glucose levels, includes a housing 12 upon which a digital readout is provided indicating the results of a body fluid test conducted by the analysis device 10. An ejection button 16 is depressed following completion of the test to eject a test strip 18 which was previously received in a loading direction "A" in housing 12. Upon depression of the ejection button 16, the test strip 18 is ejected in an ejection direction "B". The user of the test strip 18 initially inserts test strip 18 into analysis device 10 so the test strip 18 is recognized, and then removes and doses and then again manually inserts the dosed test strip 18 in the loading direction "A". After analyses, subsequent operation of ejection button 16 ejects the test strip 18. Alternately, the user can manually pull the test strip 18 in the ejection direction "B" to manually remove the test strip.

Figure 2:
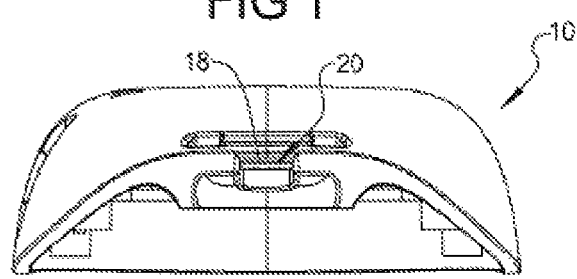
FIG. 2 shows a front elevational end view of the analysis device of FIG. 1.

Referring to FIG. 2, test strip 18 is slidably received via a test strip receiving port 20 created in a first end of analysis device 10. The test strip receiving port 20 is sized to slidably receive the test strip 18 while generally preventing twisting or rotation, such as a racking rotation, due to lateral or side-to-side displacement of the test strip.

Figure 11:
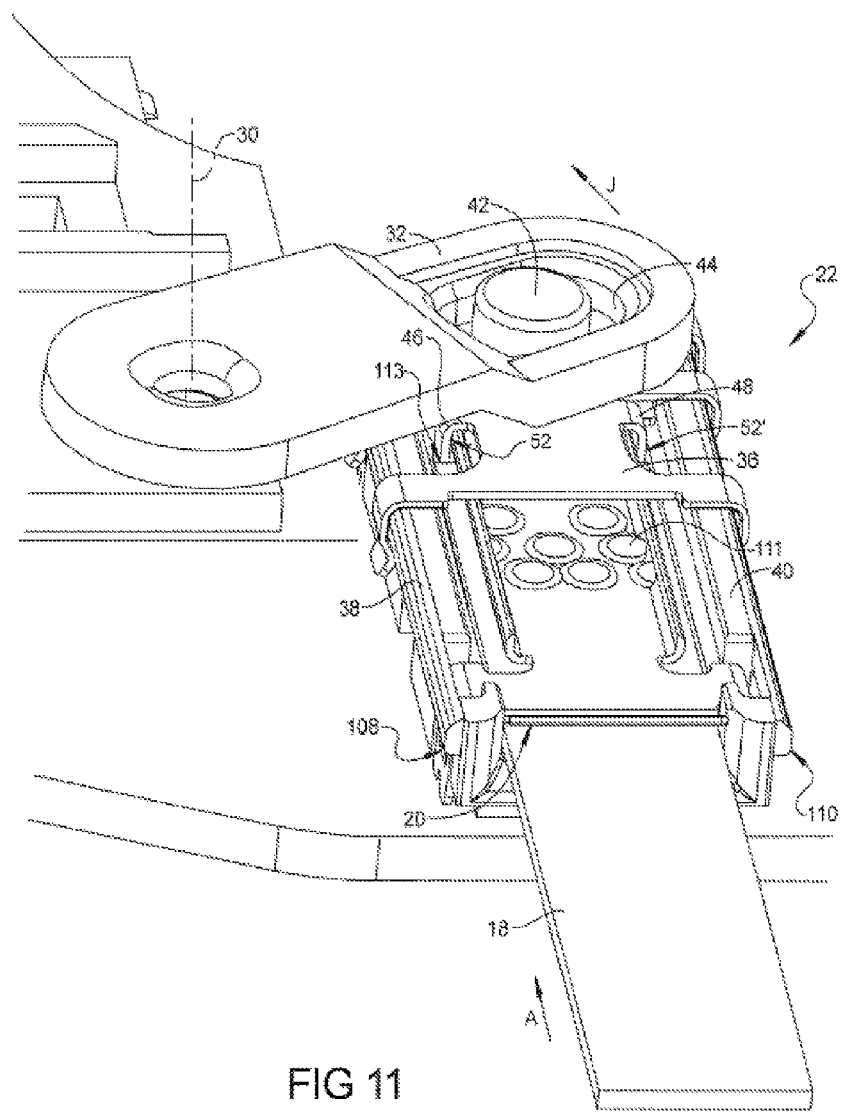
FIG. 11 shows a front left end perspective view of the test strip eject mechanism of FIG. 3.

Referring to FIG. 3 and again to FIGS. 1 and 2, with the housing 12 removed for clarity, the components of a circuit board assembly 22 are visible. Circuit board assembly 22 includes a printed circuit board 24 such as a printed circuit board having multiple components attached thereto. Housing 12 further includes a mechanism assembly 26 which can be biased prior to or upon receipt of the test strip 18 and can apply a displacement force or a biasing force to eject the test strip 18. Mechanism assembly 26 includes ejection button 16 and an axially rotatable mounting pin 28 which is rotatable with respect to a longitudinal pin center axis 30 which is affixed to a stationary component which would be on the PCB, housing, or some other nearby component. A member such as an actuator arm 32 is connected to mounting pin 28 and therefore co-rotates as mounting pin 28 axially rotates with respect to longitudinal pin center axis 30. The ejection button 16 is biased using an ejection button biasing member 34 to return to the extended position shown following depression by the user. Manual depression of ejection button 16 causes mounting pin 28 and therefore actuator arm 32 to rotate, which directly contacts and slidably displaces a sled 36 in the ejection direction "B". The sled 36 is slidably and connectably engaged with respect to opposed and parallel oriented first and second guide rails 38, 40. First and second guide rails 38, 40 are fixedly connected to printed circuit board 24. The sled 36 slides with respect to and is externally engaged to each of the first and second guide rails 38, 40, as will be better described in reference to FIGS. 11 and 12. A sled post 42 which is generally cylindrical in shape is directly and fixedly connected to sled 36 and is slidably and rotatably received within an elongated slot 44 created in actuator arm 32.

Figure 3:
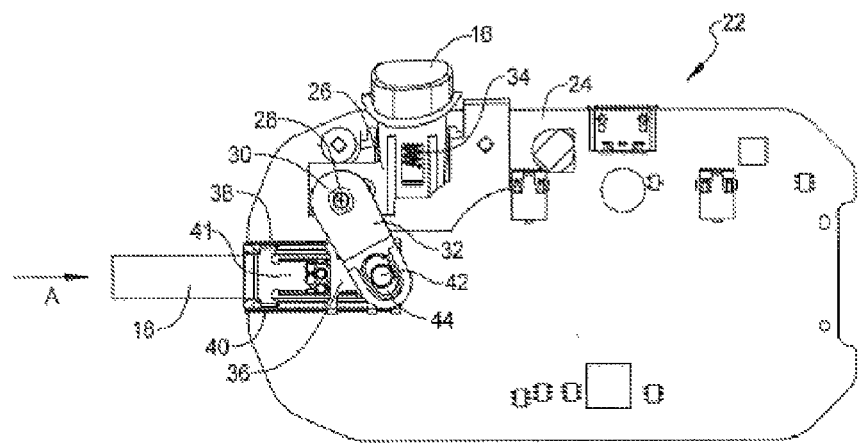
FIG. 3 shows a top plan view of a circuit board assembly and test strip ejector of the analysis device of FIG. 1, with the test strip ejector in the default/test position.

Referring to FIG. 4 and again to FIGS. 1-3, after completion of the test by the analysis device 10, the test strip 18 is ejected from housing 12 by depression of ejection button 16. Actuator arm 32 rotates in a clockwise direction, as viewed in FIG. 4, having sled post 42 engaged with sled 36 within elongated slot 44, displacing sled 36 in the ejection direction "B" and thereby discharging test strip 18. The amount of force applied by the user to ejection button 16 determines the force applied by actuator arm 32 and sled post 42 to sled 36 to eject test strip 18. The higher the applied force, the greater the velocity of ejection of test strip 18. Therefore, the force received (Fr) to eject the test strip 18 is a function of the force applied (Fa) to ejection button 16 which is greater than the opposing biasing force (Fo) of ejection button biasing member 34 (Fr=Fa−Fo). Test strip 18 can therefore be ejected with enough force/velocity to direct test strip 18 into a trash or biohazard container (not shown) when not positioned directly over the container, or if analysis device 10 is held directly over the trash or biohazard container, a reduced force applied to ejection button 16 will push test strip 18 out to subsequently fall by gravity. When ejection button 16 is released, the biasing force of ejection button biasing member 34 returns ejection button 16 to its fully extended position.

Figure 13:
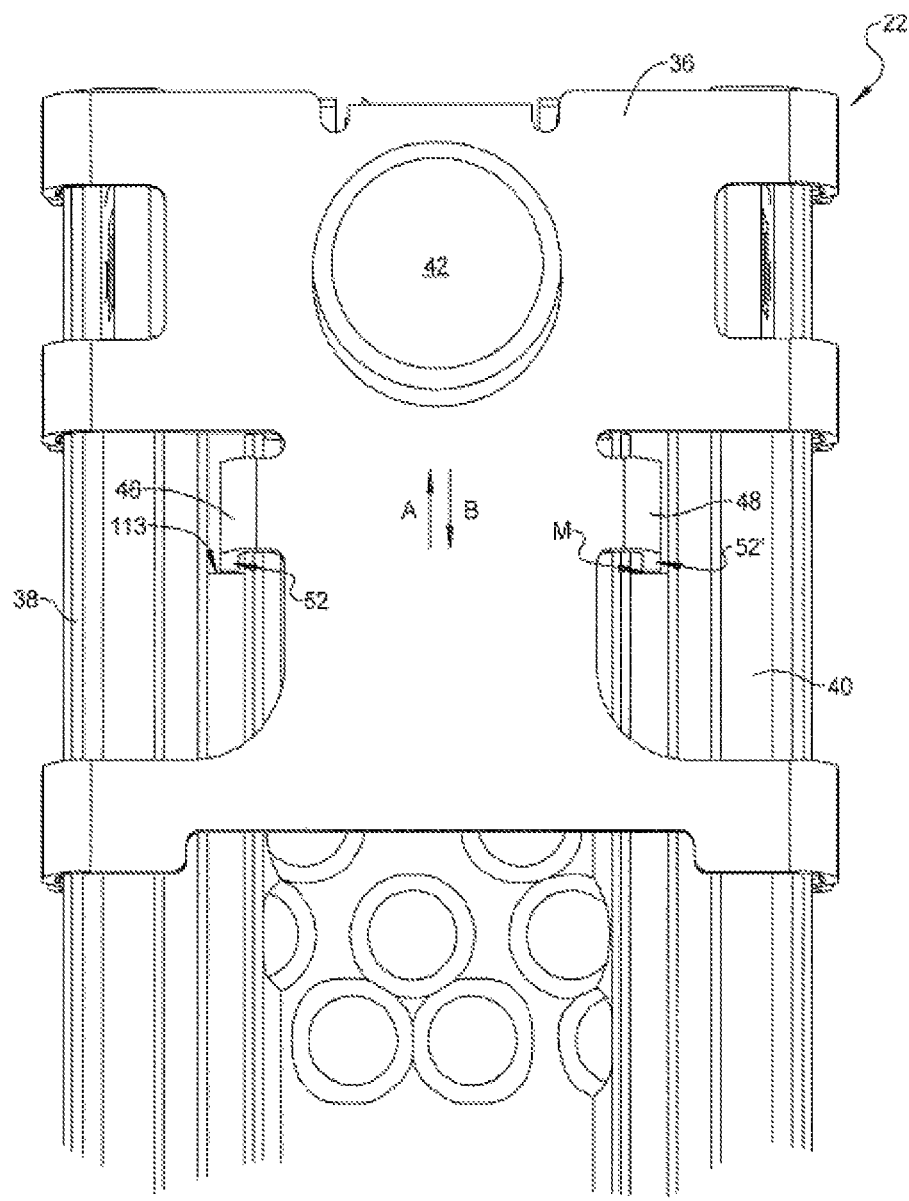
FIG. 13 shows a rear left end perspective view of the test strip eject mechanism of FIG. 12.

With continuing reference to FIG. 3, the actuator arm 32 is shown in a test strip analysis position reached by a counter-clockwise rotation with respect to longitudinal pin center axis 30. The test strip analysis position can be provided in each of two aspects. In a first aspect, in addition to biasing ejection button 16, actuator arm 32 is also normally biased by ejection button biasing member 34 to the counterclockwise rotated position shown in FIG. 3, which prepositions the actuator arm 32 and the sled 36 in a neutral position (defined in this aspect as the position shown in FIG. 3) ready for receipt of test strip 18. In this aspect, test strip 18 is freely manually loaded into housing 12 until a strip end contacts or nearly contacts the sled 36. In the neutral position of sled 36 defined in reference to the first aspect test position, it is desirable that a clearance be retained between the test strip 18 and sled 36 during the analyses phase (which is shown and described in reference to FIG. 13). After testing/analyses is complete, ejection button 16 is depressed against the biasing force of ejection button biasing member 34, causing rotation of actuator arm 32, and the sled 36 is displaced in the ejection direction "B", thereby discharging test strip 18.

Figure 4:
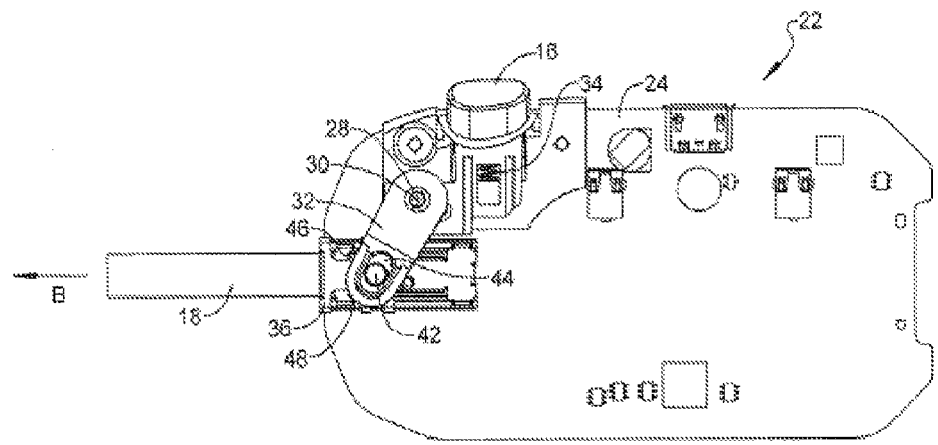
FIG. 4 shows a top plan view of the circuit board assembly and test strip ejector similar to FIG. 3, after the test strip ejector is displaced to the ejection position.

With continuing reference to FIGS. 3 and 4, the test strip analysis position shown in FIG. 3 in a second aspect is reached by displacing sled 36 in the loading direction "A" from an initial position of sled 36 as shown in FIG. 4 by manual insertion of the test strip 18. The force of insertion of test strip 18 slidably displaces sled 36 in the loading direction "A" which directly rotates the actuator arm 32 in a counter-clockwise direction. As the test strip 18 is inserted in the loading direction "A", contact between test strip 18 and sled 36 occurs in a rail cavity 41 which is created between the first and second guide rails 38, 40. The elongated slot 44 permits actuator arm 32 to rotate with respect to longitudinal pin center axis 30 in response to a load applied from a sliding motion in the loading direction "A" of both the test strip 18 and sled 36. In this aspect, the sliding motion of sled 36 is therefore translated into a rotational motion of actuator arm 32 by contact between sled post 42 and the wall of elongated slot 44.

Displacement of ejection button 16 causes rotation of the mounting pin 28 in a clockwise direction as viewed with respect to FIG. 4. As the actuator arm 32 rotates in the clockwise direction, a force is applied via contact between actuator arm 32 and sled post 42 such that the rotational motion of actuator arm 32 is translated into an axial sliding motion of test strip 18 in the ejection direction "B". The test strip 18 which is in direct contact with sled 36 is ejected in the ejection direction "B" as the sled 36 is induced to slide in the ejection direction "B". The test strip 18, during test strip loading in the second aspect described above, and during the ejection step for both aspects, is in direct contact with each of opposed first and second contact legs 46, 48 which are substantially rigid, integrally connected to sled 36, and positioned between deflectable legs which will be described in reference to FIG. 5. Test strip 18 when positioned within rail cavity 41 directly contacts first and second contact legs 46, 48 which extend from sled 36 into rail cavity 41.

Figure 5:
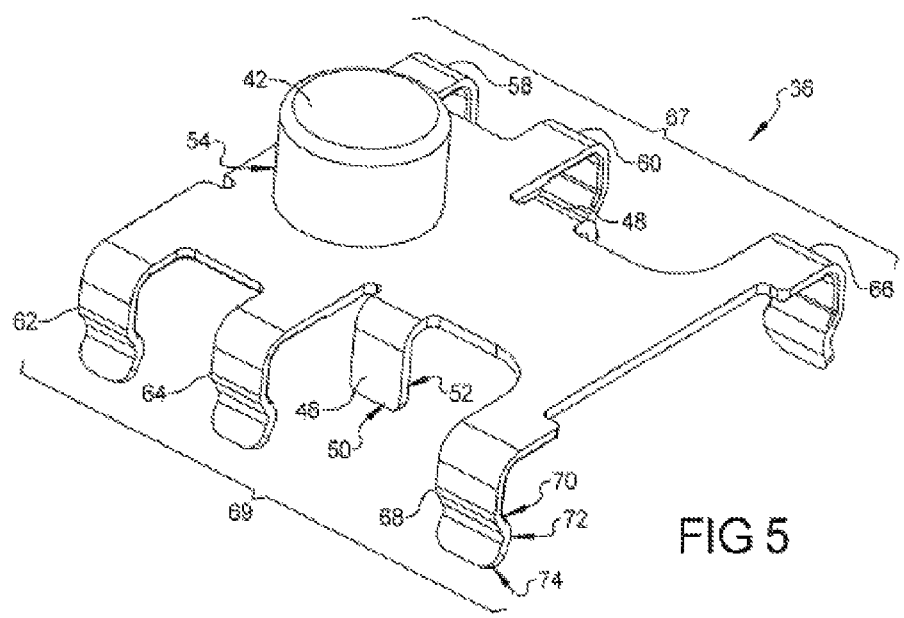
FIG. 5 shows a top front left perspective view of a test strip sled of the present disclosure.

Referring to FIG. 5, the first and second contact legs 46, 48 are oppositely positioned in a mirror image configuration of each other and have common individual features therefore, the following discussion of first contact leg 46 applies equally to second contact leg 48. First contact leg 46 is substantially rigid and includes a planar leg portion 50 having a contact face 52 facing away from sled post 42. The contact face 52 of each of the first and second contact legs 46, 48 directly contacts the test strip 18 for initially displacing the sled 36 in the loading direction "A" in the second aspect discussed herein, and for ejecting the test strip 18 from analysis device 10 in both the first and second aspects. The provision of the two spaced apart contact faces 52, 52' of the first and second contact legs 46, 48 eliminates induced torque on sled 36 that would occur using only a single contact point of a single pin or leg, therefore further reducing the chance of racking the sled 36 during ejection.

The sled post 42 has a cylindrical body 54 which is perpendicularly oriented with respect to a planar body portion 56 of sled 36. According to several embodiments, sled 36 is made of a metal such as stainless steel, to maximize a stiffness-to-weight ratio of sled 36. Other materials for sled 36 can also be used, including plastics. According to several aspects sled post 42 is created of a polymeric material having a low coefficient of friction such as polyoxymethylene (POM). A POM material or a similar material having a low coefficient of friction is selected for sled post 42 to maintain the shape of sled post 42 and to minimize frictional resistance between sled post 42 and actuator arm 32 as sled post 42 slides within elongated slot 44 and as actuator arm 32 rotates with respect to sled post 42. According to other aspects, in lieu of a separate part, sled post 42 can be an integral extension of the material of sled 36 and made such as by a staking, drawing or similar process during manufacture of sled 36. In these aspects, sled post 42 can be cylindrical, dome shaped, or other shape as the manufacturing process allows. In these aspects, it is also desirable to provide a coating of a material such as polytetrafluoroethylene (PTFE) at least on sled post 42 to minimize frictional resistance between sled post 42 and actuator arm 32.

With continuing reference to FIG. 5 and again to FIGS. 3 and 4, sled 36 includes proximately positioned first and second legs 58, 60 and oppositely proximately positioned third and fourth legs 62, 64 which are in mirror image configuration with respect to first and second legs 58, 60. The sled post 42 according to several aspects is centrally located with respect to each of the first, second, third, and fourth legs 58, 60, 62, 64. A fifth leg 66 can also be provided in a spaced apart relationship with respect to first and second legs 58, 60 such that first leg 58, second leg 60, and fifth leg 66 define a first side leg set 67. Similarly, a sixth leg 68 can be provided in a spaced apart relationship with respect to third and fourth legs 62, 64 such that third leg 62, fourth leg 64, and sixth leg 68 together define a second side leg set 69. Second side leg set 69 is a mirror image of first side leg set 67. According to several aspects, third and fourth legs 62, 64 are omitted, such that only first and second legs 58, 60 and fifth and sixth legs 66, 68 are provided to slidably engage the first and second guide rails 38, 40.

Each of the individual legs 58, 60, 62, 64, 66, 68 have a common geometry, therefore the following discussion of sixth leg 68 applies also to each of the first through fifth legs 58, 60, 62, 64, 66. Each of the legs 58, 60, 62, 64, 66, 68 is positioned oppositely about planar body portion 56 with respect to sled post 42 and is therefore oriented downwardly as viewed in FIG. 5. Each of the legs includes an inner concave leg portion 70 directly connected to an engagement portion 72 which is oppositely directed with respect to inner concave leg portion 70. Directly connected to engagement portion 72 is an end portion 74 which is oppositely directed with respect to engagement portion 72 such that inner concave leg portion 70, engagement portion 72, and end portion 74 together substantially define an S-shaped portion when viewed from an end of sled 36 as will be evident in FIG. 8. It is noted that first and second contact legs 46, 48 which are substantially rigid, are positioned, in the embodiment having six deflectable legs, between the second and fifth legs 60, 66 or the fourth and sixth legs 64, 68, and do not include any of the S-shaped portion features of inner concave leg portion 70, engagement portion 72, or end portion 74.

Referring to FIG. 6 and again to FIG. 5, sled post 42 includes a post connection end 76 which extends through planar body portion 56 such that post connection end 76 is positioned on a lower body face 78 side of planar body portion 56. Post connection end 76 can be mechanically connected to planar body portion 56 using a plurality of connection methods, including staking, forming or adhesively boding, to fix post connection end 76 with respect to planar body portion 56. In addition, a post retainer 80 can also be included with post connection end 76, which can be biased into contact with planar body portion 56 or displaced, such as by a staking operation, such that post retainer 80 acts as a retention member to further retain the fixed position of post connection end 76. According to additional embodiments, a friction reduction coating 81 made from a material having a low coefficient of friction, such as polytetrafluoroethylene (PTFE), can be provided as a coating on at least the lower body face 78 of planar body portion 56. Friction reduction coating 81 can also be provided on both sides or faces of sled 36 prior to or following formation of any of the legs.

Figure 6:
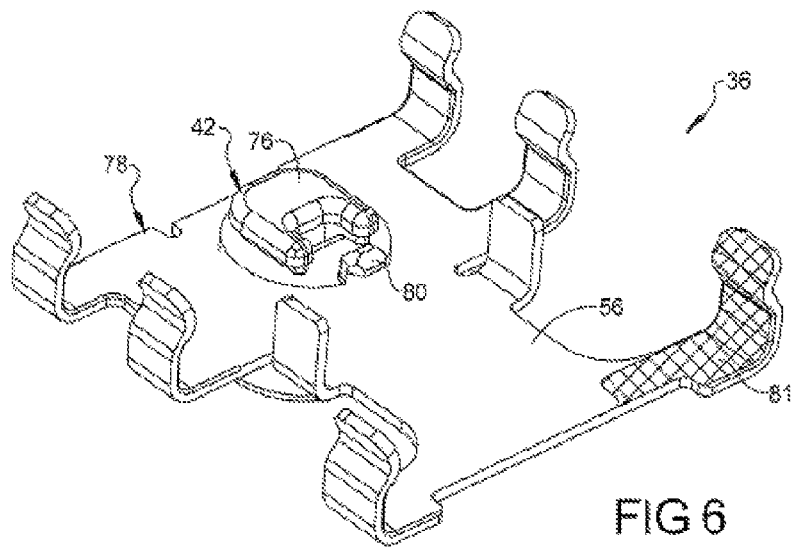
FIG. 6 shows a bottom front right perspective view of the test strip sled of FIG. 5.
Figure 7:
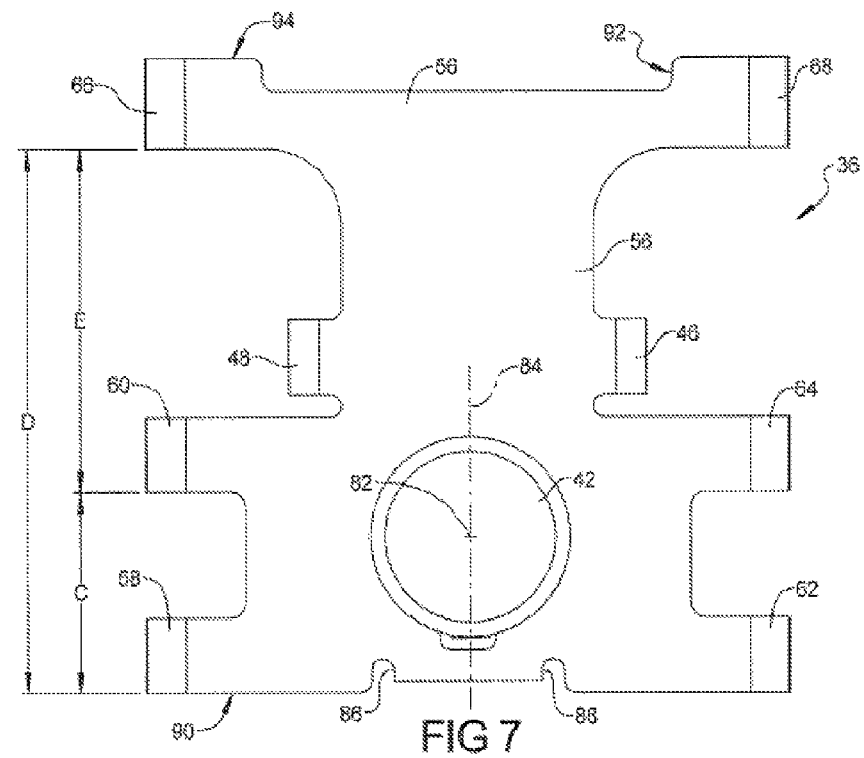
FIG. 7 shows a top plan view of the test strip sled of FIG. 5.

Referring to FIG. 7 and again to FIGS. 5-6, as previously noted sled post 42 is centrally positioned with respect to each of the first and second legs 58, 60 and third and fourth legs 62, 64 such that a longitudinal post central axis 82 of sled post 42 is aligned with a sled longitudinal axis 84. According to additional aspects, features such as first and second body notches 86, 88 can be created at a body first end 90 of planar body portion 56. First and second body notches 86, 88 define a location where material for individual sleds 36 can be perforated from a strip of material (not shown) defining multiple ones of sleds 36. In addition, a third body notch 92 can be created at a body second end 94 of planar body portion 56. The purpose for third body notch 92 will be better described in reference to FIG. 14. According to several embodiments, a first leg-to-leg spacing "C" is provided between first and second legs 58, 60 and also with respect to third and fourth legs 62, 64. A second leg-to-leg spacing "D" is provided between each of first leg 58 and third leg 62 and both fifth leg 66 and sixth leg 68, respectively. Second leg-to-leg spacing "D" is selected such that a third leg-to-leg spacing "E" between, for example, second leg 60 and fifth leg 66 is greater than first leg-to-leg spacing "C". The purpose for this increased spacing used for second leg-to-leg spacing "D" will be described in better detail in reference to FIGS. 12 and 14.

It is noted that the location of first and second contact legs 46, 48, positioned between second and fourth legs 60, 64 and fifth and sixth legs 66, 68, can be positioned at any distance with respect to longitudinal post central axis 82, however, to help mitigate against a racking or rotation motion of sled 36 during operation, the first and second contact legs 46, 48 are positioned as close as possible with respect to longitudinal post central axis 82, while providing clearance for die or stamp tooling during creation of these legs. Racking is defined herein as axial rotation of sled 36 with respect to longitudinal post central axis 82, which if occurring could cause the sled 36 to bind during sliding travel on the first and second guide rails 38, 40, or cause frictional resistance to sliding displacement, particularly during test strip ejection operation when rapid sliding motion is desired. It is noted the description of the legs as first, second, third, fourth, fifth, and sixth legs is for clarity in collectively describing all six of the legs according to one embodiment, however, the legs on any one side of sled 36 such as legs 58, 60, 66 can also be referred to as first, second and third legs in defining their order.

Referring to FIG. 8 and again to FIGS. 3 and 5-7, sled post 42 and its longitudinal post central axis 82 are oriented substantially perpendicular with respect to a body upper surface 96 of planar body portion 56. Each of the first and second contact legs 46, 48 are oriented substantially parallel with respect to longitudinal post central axis 82 and therefore are oriented substantially perpendicular with respect to body upper surface 96 and lower body face 78. Each of the first through sixth legs 58, 60, 62, 64, 66, 68 have similar features with respect to first and third legs 58, 62 shown, therefore the following discussion applies equally to each of the first through sixth legs. A first upper contact surface 98 is defined in inner concave leg portion 70', and an oppositely located second upper contact surface 100 is provided with inner concave leg portion 70" such that an upper contact surface spacing dimension "G" is defined between first and second upper contact surfaces 98, 100. A first lower contact surface 102 is provided with inner concave leg portion 70', and an oppositely positioned second lower contact surface 104 is provided with inner concave leg portion 70". A lower contact surface spacing dimension "H" is greater than the upper contact surface spacing dimension "G", thereby defining an outwardly canted angle α for inner concave leg portion 70" which is duplicated but oppositely directed with respect to inner concave leg portion 70". The difference between upper and lower contact surface spacing dimensions "G", "H" helps prevent binding of the individual legs during sliding motion of sled 36. A spacing or distance dimension between engagement portions 72', 72" is less than each of the upper or lower contact surface spacing dimensions "G", "H". The S-shape of each of the legs 58, 60, 62, 64, 66, 68 including engagement portion 72 externally contacts and captures one of the guide rails 38, 40, which together with the deflectable design of the legs thereby provides continuous, positive contact between the legs with the guide rails 38, 40 throughout the travel path of sled 36, and limiting displacement of the sled 36 to only sliding motion in either the loading direction "A" or the opposite ejection direction "B", and further preventing the sled 36 from moving away from the guide rails 38, 40 during sliding motion.

Referring to FIG. 9 and again to FIG. 3, sled 36 is shown in the test strip 18 loaded or test/analysis position such that a plane 106 extending through planar body portion 56 of sled 36 is oriented parallel to each of test strip 18 and printed circuit board 24. Actuator arm 32 rotates parallel with respect to plane 106, which therefore minimizes the potential for binding or racking of sled 36 as it receives or ejects test strip 18.

Figure 9:
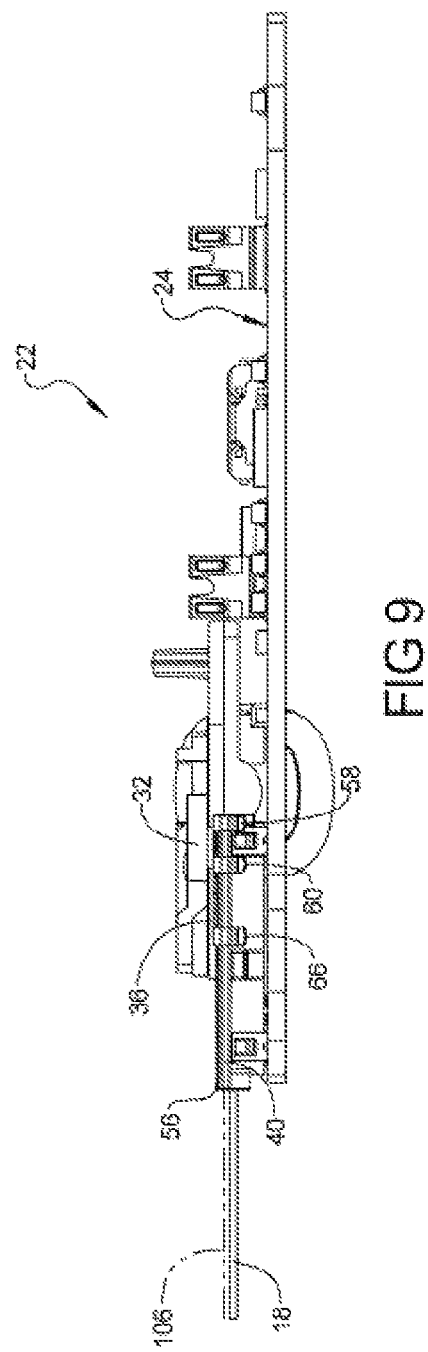
FIG. 9 shows a side elevation view of the circuit board assembly of FIG. 3.

Referring to FIG. 10 and again to FIGS. 3 and 9, as test strip 18 is slidably moved within rail cavity 41, sled 36 is free to slidably displace either toward or away from the viewer, as shown in reference to FIG. 10. Sled 36 is slidable but is contained with respect to a "Z" axis by sliding engagement of inner concave leg portion 70' with respect to a first guide rail bulbous face 108 of first guide rail 38, and with respect to inner concave leg portion 70" by sliding engagement with respect to a second guide rail bulbous face 110 of second guide rail 40. Each of the first and second guide rails 38, 40 are oriented substantially perpendicular with respect to a board planar surface 112 of printed circuit board 24.

Figure 10:
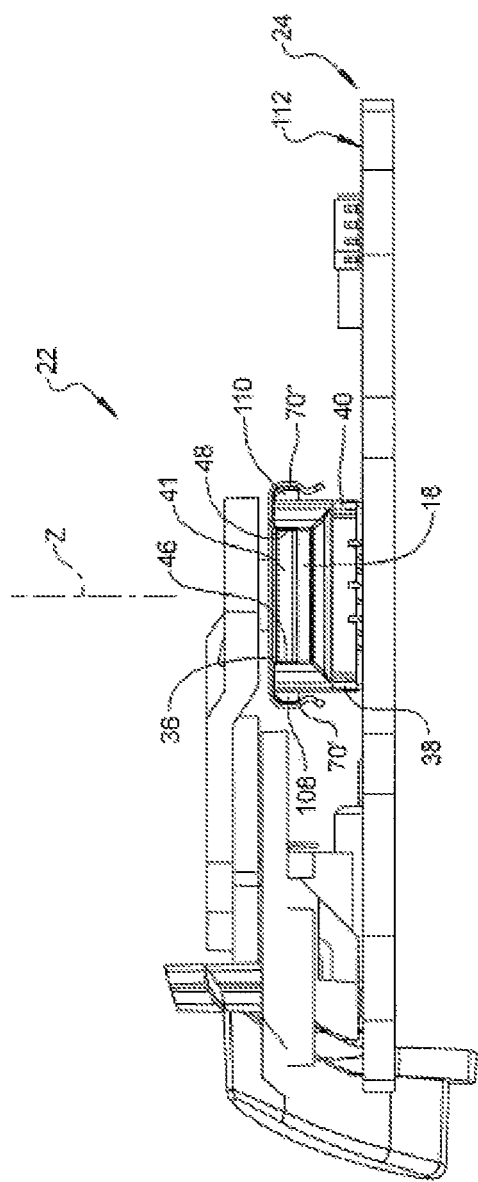
FIG. 10 shows a front end elevation view of the circuit board assembly of FIG. 3.

Referring to FIG. 11 and again to FIGS. 3 and 10, according to the second aspect described herein, as test strip 18 is slidably disposed into the test strip receiving port 20 in the loading direction "A", a test strip end wall 113 of test strip 18 directly contacts each of the contact faces 52, 52' of first and second contact legs 46, 48. This direct contact thereafter slidably displaces sled 36 also in the loading direction "A". As sled post 42 of sled 36 is displaced in the loading direction "A", sled post 42 contacts actuator arm 32 in elongated slot 44 and thereby rotates actuator arm 32 in a loading rotational direction "J" with respect to the longitudinal pin center axis 30. For both the first and second aspects, as test strip 18 is received at the test position shown, multiple contact points of the test strip 18 contact a connector 111 positioned in the device, thereby making electrical contact with the connector 111 to permit analyses of the fluid provided with test strip 18. Connector 111 can include multiple, individual contact points that each align with one of the contact points of the test strip 18.

Figure 12:
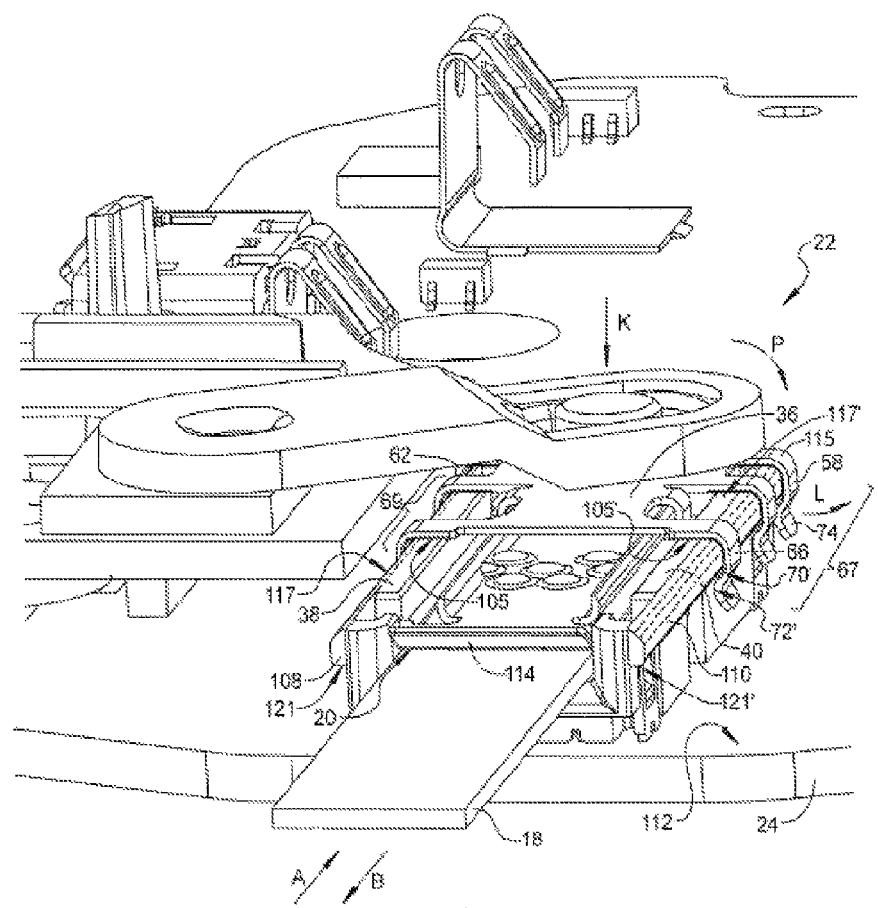
FIG. 12 shows a front right end perspective view of the test strip eject mechanism of FIG. 3.

Referring to FIG. 12, a closure member 114 is provided between first and second guide rails 38, 40 and delineates test strip receiving port 20, and further maintains parallel alignment between test strip 18 and board planar surface 112. Each of the first through sixth legs 58, 60, 62, 64, 66, 68 of sled 36 is positioned having the planar leg faces 105, 105' in sliding contact with upper surfaces 117, 117' of the first and second guide rails 38, 40, and each includes a convex leg portion 115 wrapping partially about the first and second guide rail bulbous faces 108, 110, thereby individually externally connecting each of the first through sixth legs 58, 60, 62, 64, 66, 68 to one the first or second guide rails 38, 40. The inner concave leg portion 70 of each of the first through sixth legs is in sliding contact with an oppositely facing lower surface 121, 121' of either the first or second guide rail bulbous face 108, 110 such that the first through sixth legs 58, 60, 62, 64, 66, 68 partially capture one of the first or second guide rails 38, 40. This partial capture prevents sled 36 from lifting off in a direction perpendicular to the first and second guide rails 38, 40, and prevents the planar leg faces 105, 105' from moving away from sliding contact with the upper surfaces 117, 117' of the first or second guide rails 38, 40 at any position of the sled 36. The engagement portions 72 of each of the first through sixth legs 58, 60, 62, 64, 66, 68 are also positioned in sliding contact with one of the lower surfaces 121, 121' of the first or second guide rail bulbous faces 108, 110 to further mitigate lifting of the sled 36 at any of its sliding positions.

It is noted that the multiple independent legs herein described as first through sixth legs 58, 60, 62, 64, 66, 68 are included in one embodiment of sled 36 however, according to further embodiments, any or all of the individual legs of either first or second side leg sets 67, 69 can be combined together and still include the features of inner concave leg portion 70 and engagement portion 72. Therefore, a single leg, two legs, three legs or more than three deflectable legs can be provided on each side of sled 36. The width and/or dimensions of the single leg or multiple legs on each side can also be varied. For example only, a single leg having a width corresponding to the outside end to outside end spacing of first and fifth legs 58 and 66 can be used in place of first leg 58, second leg 60 and fifth leg 66. The use of multiple individual legs in place of single wide legs reduces surface leg area sliding friction of sled 36 while providing maximum spacing between the end legs, such as first leg 58 and fifth leg 66, which maximizes a moment arm of sled 36, thereby minimizing a racking or rotation of sled 36 as it slides with respect to the first or second guide rails 38, 40. A further advantage of providing the multiple individual legs of the first and second side leg sets 67, 69 is that multiple individual legs provide greater elastic flexibility than single or combined legs. This elastic flexibility allows sled 36 to be mounted during an installation stage in a sled installation direction "K" oriented perpendicular to the first and second guide rails 38, 40, rather than requiring sliding installation in either of the loading direction "A" or ejection direction "B". The legs 58, 60, 62, 64, 66, 68 outwardly elastically deflect about the first and second guide rails 38, 40 allowing installation of the sled 36 in sled installation direction "K" transverse to the loading direction "A" and the ejection direction "B".

Installation via sled installation direction "K" allows sled 36 to be positioned directly over first and second guide rails 38, 40 and installed prior to installation of actuator arm 32 without interfering with any other component mounted on printed circuit board 24, or requiring the other component or components to be temporarily removed and/or installed at a later time than the installation of sled 36. This allows for automated machine installation of sled 36. During installation of sled 36 in the sled installation direction "K", the end portion 74 of each of the individual legs deflects elastically outward with respect to the first or second guide rail bulbous face 108, 110. This allows each leg to elastically deflect in a leg displacement direction "L", as shown for first side leg set 67, and oppositely deflect (not visible in this view) with respect to second side leg set 69. When the engagement portion 72, 72' moves past the first or second guide rail bulbous face 108, 110, the leg elastically snaps back to the non-deflected position. With the engagement portion 72, 72' oppositely positioned about the first or second guide rail bulbous face 108, 110 with respect to the planar leg faces 105, 105', the sled 36 is thereby slidably coupled to the first and second guide rails 38, 40, limiting motion of sled 36 to sliding motion in either of the loading or ejection directions "A", "B".

Referring to FIG. 13 and again to FIG. 12, in the neutral position of sled 36 defined in reference to both the first and second aspects discussed above, test strip 18 is positioned in the fully inserted or test position. A clearance "M" can be provided between the test strip end wall 113 of test strip 18 and the contact faces 52, 52' of first and second contact legs 46, 48 of sled 36 during the test/analyses phase. Provision of clearance "M" prevents any force being applied to test strip 18 in the ejection direction "B" during the test/analysis phase.

Referring to FIG. 14 and again to FIGS. 3-12, third body notch 92 provides clearance for angled entrance lip 116 when sled 36 reaches its furthest displaced ejection position. Although contact between third body notch 92 and angled entrance lip 116 can provide a positive stop for sled 36, according to several aspects, a preferred positive stop for sled 36 is provided by direct contact between first and second contact legs 46, 48 and each of a first and second stop face 118, 119 provided with closure member 114. Following depression of ejection button 16, actuator arm 32 rotates in an ejection rotational direction "N", thereby creating direct contact between a slot wall 120 of elongated slot 44 and an outer or perimeter surface of sled post 42. This contact and counterclockwise rotation of actuator arm 32 displaces sled 36 in the ejection direction "B", allowing ejection or removal of test strip 18. It is noted that sled 36 is prevented from extending past either end of the first or second guide rails 38, 40 by the positive stops created using first and second stop faces 118, 119 and oppositely by contact between first and second contact legs 46, 48 and each of a first and second abutment face 126, 127 provided with a cover plate 128 seated between first and second guide rails 38, 40. Sled 36 therefore cannot extend past rail assembly first end 122 or an opposite rail assembly second end 124 due to the positive stop features. According to other aspects, it is possible to eliminate the positive stop features and prevent displacement of sled 36 past either rail assembly first or second ends 122, 124 by limiting a rotation of mounting pin 28, and thereby limiting rotation of actuator arm 32 between the fully ejected position and the fully loaded position of sled 36.

Figure 8:
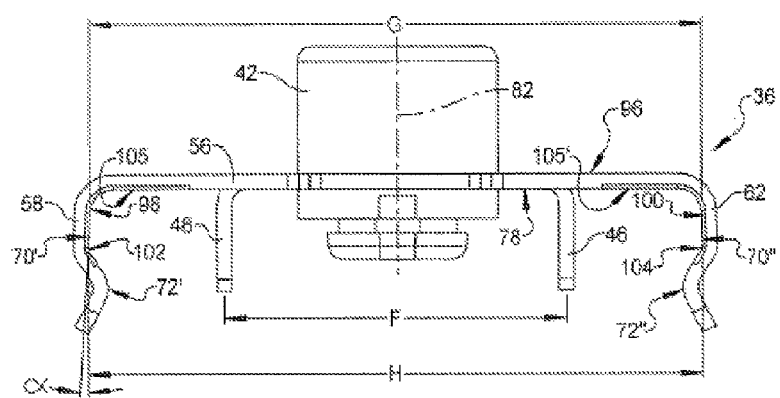
FIG. 8 shows an end elevation view of the test strip sled of FIG. 5.
Figure 14:
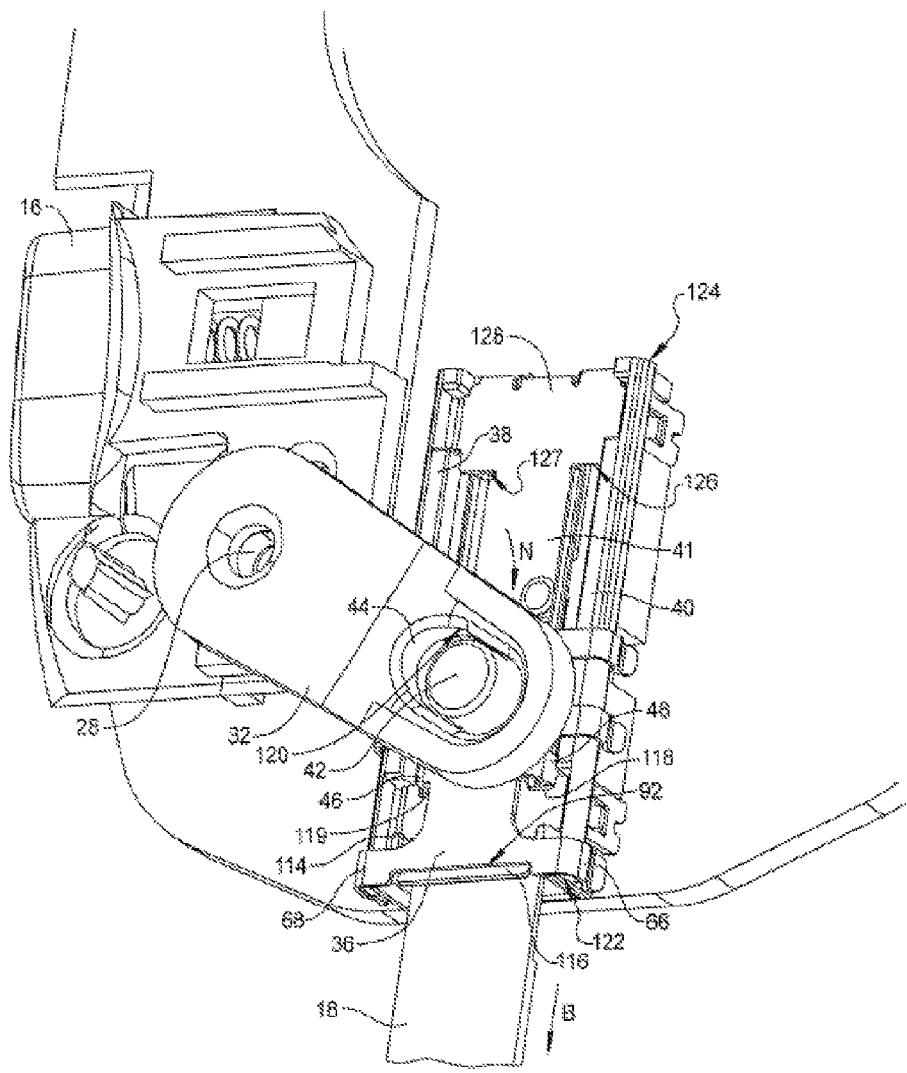
FIG. 14 shows a front right end perspective view of the test strip eject mechanism of FIG. 4.

With continuing reference to FIGS. 8 and 14, the contact leg spacing dimension "F" of first and second contact legs 46, 48 is selected to position first and second contact legs 46, 48 within rail cavity 41 while providing as wide as possible contact leg spacing dimension "F" at the maximum width of test strip 18. This also helps mitigate rotation or racking of sled 36 and/or test strip 18.

For operation, the test strip ejector system 11 for receiving and ejecting test strip 18 from fluid analysis device 10 includes first and second guide rails 38, 40 defining rail cavity 41 between the guide rails 38, 40. Sled 36 includes first and second spatially separated contact faces 52, 52' positioned in the rail cavity 41 and opposed first and second legs 58, 62, each of the legs 58, 62 connected externally to and slidably coupled with respect to one of the first or second guide rails 38, 40 for sled motion in each of the loading direction "A" and the ejection direction "B". Actuator arm 32 is rotatably connected to the fluid analysis device 10. The sled 36 is coupled to the actuator arm 32 such that rotation of the actuator arm 32 in the loading rotational direction "J" moves the sled in the loading direction "A" to position the sled 36 in the test strip test position (shown in FIG. 3). Opposite rotation of the actuator arm 32 in the ejection rotational direction "P" operates to displace the sled 36 in the ejection direction "B" away from the test strip test position and to position the first and second contact faces 52, 52' in direct contact with the test strip 18 to eject the test strip 18 from the fluid analysis device 10.

Referring to FIG. 15 and again to FIGS. 1-14, an analysis device 130 is modified from analysis device 10 to include a sled 132 having four legs in lieu of six legs, including first, second, third and fourth legs 134, 136, 138, 140 which are substantially equivalent to first, third, fifth and sixth legs 58, 62, 66 and 68 of sled 36. The first and second guide rails 38, 40 are removed for clarity. The sled post 42 of sled 132 is rotatably connected to actuator arm 32. First and second contact legs 142, 144 are similarly provided and oriented on sled 132 and therefore perform the same functions as first and second contact legs 46, 48. A raised member 146 extending from housing 12 includes an arc-shaped surface 148 which is directly contacted by sled post 42 and acts as a guide for sled post 42 during displacement of sled 132. The mounting pin 28 is slidably received in a first elongated slot 150 created in an ejection button body extension 152 which is connected to ejection button 16. In the sled neutral position shown, ejection button 16 and ejection button biasing member 34 are fully extended, mounting pin 28 is positioned proximate to a first end of first elongated slot 150, and sled 132 is positioned to receive a test strip 18. A driver pivot pin 154 extends from actuator arm 32, and according to several embodiments is integrally connected to actuator arm 32. Driver pin 154 is received in a second elongated slot 156 created in body extension 152, having a shorter length than first elongated slot 150 to allow limited displacement of driver pin 154 during rotation of actuator arm 32. A stop member 158 connected to structure of housing 12 provides a non-displaceable receiving point for ejection button biasing member 34.

Figure 15:
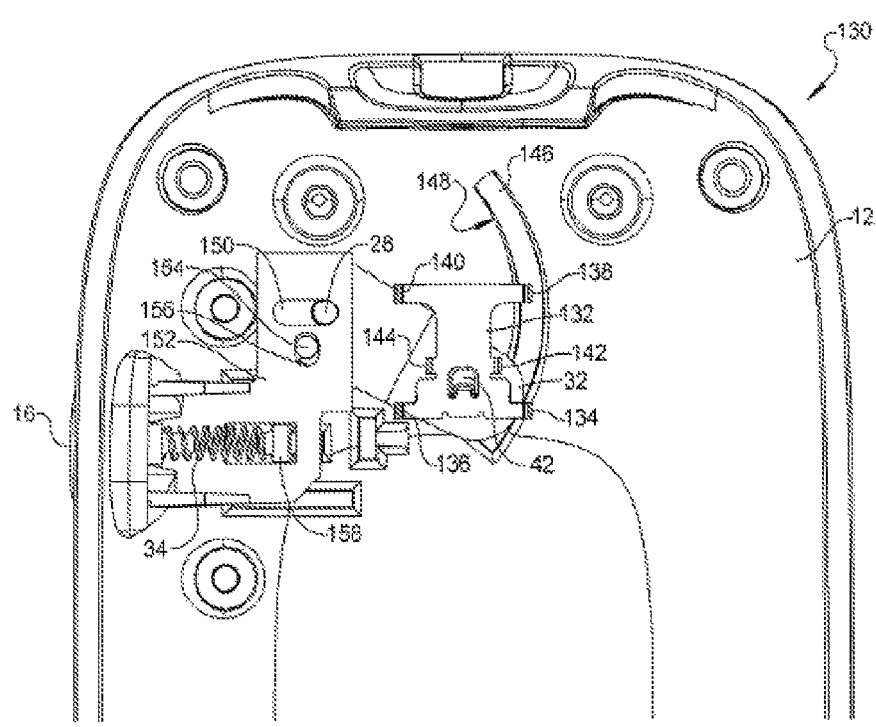
FIG. 15 shows a bottom plan view of a circuit board assembly and test strip ejector modified from the analysis device of FIG. 1, with the test strip ejector in the default/test or neutral position.
Figure 16:
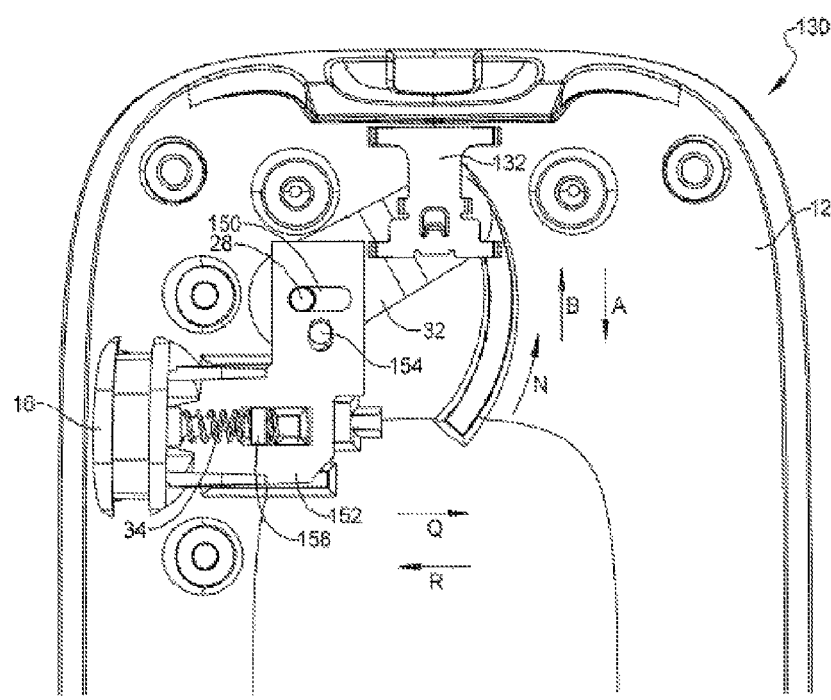
FIG. 16 shows a bottom plan view of the circuit board assembly and test strip ejector similar to FIG. 15, after the test strip ejector is displaced to the ejection position.

Referring to FIG. 16 and again to FIG. 15, ejection button 16 is shown after depression which compresses ejection button biasing member 34 against stop member 158 and slidably displaces ejection button 16 and body extension 152 in a release direction "Q". This motion of body extension 152 also displaces driver pin 154 in the release direction "Q". Because mounting pin 28 is substantially fixed with respect to housing 12, displacement of driver pin 154 in the release direction "Q" rotates actuator arm 32 in the ejection rotational direction "N". Displacement in the release direction "Q" continues until, by the displacement of body extension 152, a second end of first elongated slot 150 is positioned proximate to mounting pin 28 and the positions of mounting pin 28 and driver pin 154 are reversed with respect to their positions in the neutral position shown in FIG. 15. Rotation of actuator arm 32 in the ejection rotational direction "N" displaces sled 132 in the ejection direction "B". Subsequent release of ejection button 16 by the user allows the biasing force of ejection button biasing member 34 to displace body extension 152 and ejection button 16 in a return direction "R", opposite to release direction "Q", thereby returning sled 132 in the loading direction "A" to the neutral position shown in FIG. 15.

As noted herein, test strip ejectors and systems of the present disclosure can be used in meters by individual users having personal test meters. Test strip ejector systems of the present disclosure can also be incorporated in commercial devices such as hospital meters, for example rechargeable test meters recharged by installation in a base unit, and/or blood glucose meters such as ACCU-CHEK® Inform System glucose meters manufactured by Roche Diagnostics. The test strips used by such hospital and glucose test meters can be configured differently from the test strips identified herein to conform to the requirements of the test and/or test meter, however the test strip ejector systems of the present disclosure will be similarly configured and function in a similar manner.

In addition, test strip ejectors and systems of the present disclosure can also be incorporated in individual or commercial devices such as blood coagulant test meters, for example blood clotting time test meters such as the CoaguChek® XS System coagulant test meters manufactured by Roche Diagnostics. The test strips used by such blood coagulant test meters can be configured differently from the test strips identified herein to conform to the requirements of the test and/or test meter, however the test strip ejector systems of the present disclosure will be similarly configured and function in a similar manner.

Test strip ejectors of the present disclosure offer several advantages. The following discussion of analysis device 10 applies equally to analysis device 130. Sled 36 of the present disclosure provides a sliding motion member that is retained by its deflectable legs externally to a parallel set of guide rails 38, 40. This provides a clear space or rail cavity 41 between the guide rails for sliding motion of the test strip 18 in direct contact with sled 36. The first and second contact legs 46, 48 of sled 36 extend into rail cavity 41 so continuous contact with test strip 18 is maintained when test strip 18 is positioned in rail cavity 41 during sliding motion, at least in the ejection direction "B". In the neutral position of sled 36 defined in reference to the first aspect test position, a clearance "M" can be maintained between the test strip 18 and sled 36 during the analyses phase to prevent any force being applied to test strip 18 in the ejection direction "B" during the test/analysis phase. According to other aspects, continuous contact between first and second contact legs 46, 48 of sled 36 with test strip 18 can be maintained during all times when test strip 18 is positioned in rail cavity 41. The use of multiple elastically flexible legs 58, 60, 62, 64, 66, 68 extends a moment arm of sled 36 to minimize racking motion while also allowing for installation of sled 36 in a "Z" axis, perpendicular to the orientation of the guide rails. The sled post 42 being received in an elongated slot of actuator arm 32 converts a rotational motion of actuator arm 32 into the sliding motion of sled 36, minimizing the space required for the ejection mechanism assembly 26 on printed circuit board 24, while allowing the ejection mechanism assembly 26 to be mounted to a side of the guide rails in lieu of in axial relationship with the guide rails.

Figure 17:
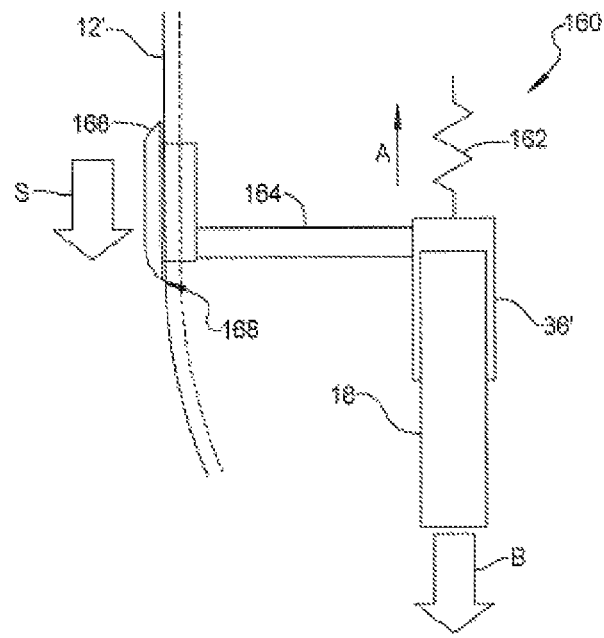
FIG. 17 shows a top plan view of another aspect for a slider test strip ejection mechanism.

Referring to FIG. 17 and again to FIGS. 1-5, with the housing 12' substantially removed for clarity, a mechanism assembly 160 is modified from mechanism assembly 26 and can be biased prior to or upon receipt of the test strip 18, and can apply a displacement force or a biasing force to either eject the test strip 18, or to retract sled 36' after an ejection operation. The sled 36' is slidably and connectably engaged with respect to opposed and parallel oriented first and second guide rails 38, 40 as previously described herein, which are not shown in FIG. 17 for clarity. In the aspect shown in FIG. 17, mechanism assembly 160 includes a biasing member 162 such as a tension spring that is biased/extended during ejection of the test strip 18, thereby creating a biasing force acting in the loading direction "A". The biasing member 162 can be directly connected to sled 36'. Sled 36' in turn is directly and non-rotatably connected to a first end of a member such as an actuator arm 164 which is a beam structure having longitudinal rigidity to retain a longitudinal shape during operation under both the biasing load of biasing member 162 and a load manually applied by a user. Actuator arm 164 is directly connected at an opposite second end to an ejection button 166 which is slidably connected to housing 12' using an outwardly extending button portion 168. Mechanism assembly 26 is shown in the test strip loaded/test position having the biasing force of biasing member 162 acting in the loading direction "A" to retain sled 36' and actuator arm 164 in the test position. A test strip 18 is manually loaded in the loading direction "A" when desired and the loading operation does not displace members of mechanism assembly 160.

When ejection of test strip 18 is desired, the user manually displaces ejection button 166 in a sliding direction "S" which is parallel with the ejection direction "B". The velocity imparted to ejection button 166 by the user determines the velocity of discharge of test strip 18. As ejection button 166 is displaced in the sliding direction "S", actuator arm 164 is directly displaced, together with sled 36' in the ejection direction "B", thereby displacing test strip 18 and simultaneously extending biasing member 162, creating a return biasing force in biasing member 162. When the user releases ejection button 166, the biasing force of extended biasing member 162 retracts sled 36', actuator arm 164, and ejection button 166 in the loading direction "A" to the initial or test position shown, awaiting manual insertion of a next test strip.

Figure 18:
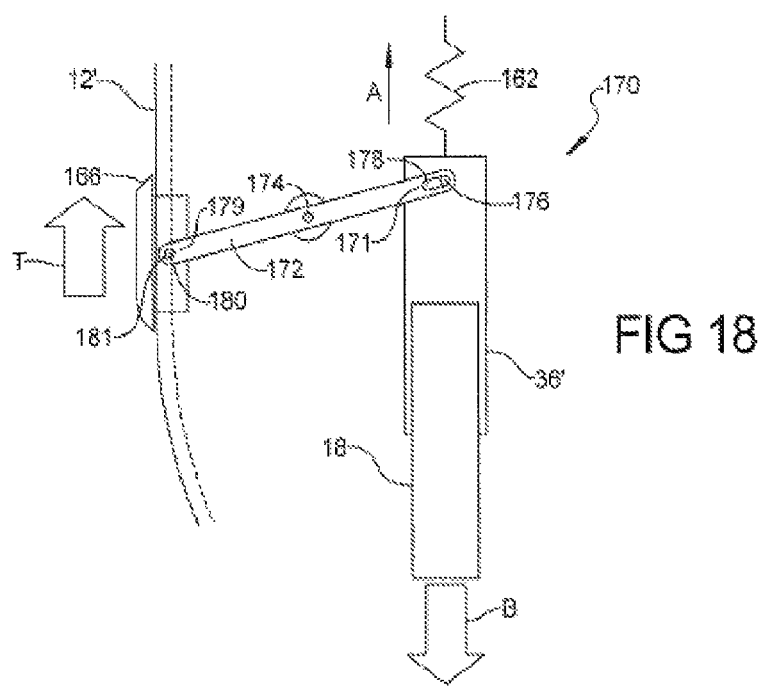
FIG. 18 shows a top plan view of another aspect for a fulcrum operated test strip ejection mechanism.

Referring to FIG. 18 and again to FIGS. 1-5 and 17, with the housing 12' again substantially removed for clarity, a mechanism assembly 170 is modified from mechanism assembly 160 and can be biased prior to or upon receipt of the test strip 18, and can apply a displacement force or a biasing force to either eject the test strip 18, or to retract sled 36' after an ejection operation. The sled 36' is slidably and connectably engaged with respect to opposed and parallel oriented first and second guide rails 38, 40 as previously described herein, which are not shown in FIG. 18 for clarity. In the aspect shown in FIG. 18, mechanism assembly 170 includes biasing member 162 acting as a tension spring that is biased/extended during ejection of the test strip 18, thereby creating a biasing force acting in the loading direction "A". The biasing member 162 can be directly connected to sled 36'. Sled 36' in turn is rotatably connected to a first end 171 of a fulcrum member such as an actuator arm 172 which is a beam structure having longitudinal rigidity to retain a longitudinal shape during operation under both the biasing load of biasing member 162 and a load manually applied by a user. Actuator arm 172 is rotatably mounted to structure of housing 12' or to printed circuit board 24 using a mounting pin 174. The first end 171 of actuator arm 172 slidably receives a first pin 176 connected to sled 36' in an elongated slot 178 of actuator arm 172. The elongated slot allows sliding motion of sled 36' as actuator arm 172 rotates about mounting pin 174. A second end 179 of actuator arm 172 oppositely positioned with respect to the first end 171 is rotatably connected to ejection button 166 using a second pin 180 extending from ejection button 166 that is received in an aperture 181 created in the second end 179 of actuator 172 sized to only rotatably receive second pin 180.

The use of mounting pin 174 provides for an opposite direction of displacement of ejection button 166 to eject test strip 18 compared to mechanism assembly 160. When ejection of test strip 18 is desired, the user manually displaces ejection button 166 in a sliding direction "T" which is opposite to sliding direction "S", and parallel with the ejection direction "B". Similar to mechanism assembly 160, the velocity imparted to ejection button 166 by the user determines the velocity of discharge of test strip 18. As ejection button 166 is displaced in the sliding direction "T", actuator arm 172 is directly rotated about mounting pin 174 (in a clockwise direction as viewed in FIG. 18), transferring a force applied through second pin 180 to first pin 176 to displace sled 36' in the ejection direction "B". This rotation of actuator arm 172 displaces test strip 18 and simultaneously extends biasing member 162, creating a return biasing force in biasing member 162. When the user releases ejection button 166, the biasing force of extended biasing member 162 retracts sled 36', oppositely rotates actuator arm 172 (in a counterclockwise direction as viewed in FIG. 18), and returns ejection button 166 parallel to the ejection direction "B" to the initial or test position shown, awaiting manual insertion of a next test strip. It is noted that the location or position of mounting pin 174 along the length of actuator arm 172 can increase or decrease the force applied to sled 36'. For example, with mounting pin 174 substantially centrally positioned in actuator arm 172 as shown, the amount of displacement of ejection button 166 substantially equals the amount of displacement of sled 36'. If mounting pin 174 is moved closer to first pin 176, a greater longitudinal displacement of ejection button 166 would be required to achieve the same displacement of sled 36'. This also results in a lower force requirement by the user to displace sled 36' due to the mechanical advantage gained. Conversely, if mounting pin 174 is moved closer to second pin 180, a lesser longitudinal displacement of ejection button 166 would be required to achieve the same displacement of sled 36'. This also necessitates a greater force requirement by the user to displace sled 36' due to the mechanical advantage lost, but can increase a velocity of displacement of test strip 18.

Referring to FIG. 19 and again to FIGS. 1-5 and 17-18, with the housing 12' again substantially removed for clarity, a mechanism assembly 182 is modified from mechanism assembly 160 to include a push rod 184 and a modified sled 185, and can be biased prior to or upon receipt of the test strip 18, and can apply a displacement force or a biasing force to either eject the test strip 18, or to retract sled 185 after an ejection operation. The sled 185, similar to sled 36, can be slidably and connectably engaged with respect to opposed and parallel oriented first and second guide rails 38, 40 as previously described herein, which are not shown in FIG. 19 for clarity. In the aspect shown in FIG. 19, mechanism assembly 182 includes biasing member 162 such as a tension spring that is biased/extended during ejection of the test strip 18, thereby creating a biasing force acting in the loading direction "A" to retain sled 185 in the test strip test position shown. The biasing member 162 can be directly connected to sled 185. Sled 185 in turn is connected to a first end 186 of the member or actuator arm 184 using a drive pin 187. Actuator arm 184 is a beam structure having longitudinal rigidity to retain a longitudinal and axial shape during operation under both the biasing load of biasing member 162 and a load manually applied by a user. Actuator arm 184 is directly connected at an opposite second end 188 to an ejection button 190 which is displaceable from the normal or test position shown by manual displacement in an inward direction "U". Mechanism assembly 182 is shown in the test strip loaded/test position having the biasing force of biasing member 162 acting in the loading direction "A" to retain sled 185 and actuator arm 184 in the test position. A test strip 18 is manually loaded in the loading direction "A" when desired and the loading operation does not displace members of mechanism assembly 182.

When ejection of test strip 18 is desired, the user manually displaces ejection button 190 in the inward direction "U" which is oriented perpendicular to the ejection direction "B". The velocity/force imparted to ejection button 190 by the user determines the velocity of discharge of test strip 18. As ejection button 190 is displaced in the inward direction "U", actuator arm 184 is directly inwardly displaced further into housing 12'. The drive pin 187 which is directly and fixedly connected to first end 186 of actuator arm 184 is slidably received in an elongated slot 192 created in sled 185. Elongated slot 192 is oriented at an angle β with respect to a longitudinal central axis 194 of sled 185. As ejection button 190 is displaced in the inward direction "U", drive pin 187 displaces from a first end of elongated slot 192 toward an opposite end of elongated slot 192. The force imparted by drive pin 187 to the wall of elongated slot 192 causes axial displacement of sled 185 in the ejection direction "B", thereby displacing test strip 18 and simultaneously extending biasing member 162, creating a return biasing force in biasing member 162. When the user releases ejection button 190, the biasing force of extended biasing member 162 retracts sled 185 in the loading direction "A" to the initial or test position shown, awaiting manual insertion of a next test strip. This motion of sled 185 acts on drive pin 187 which slides from the second to the first end of elongated slot 192 to outwardly displace both actuator arm 184 and ejection button 190. It is noted that angle β can range between approximately 20 to 60 degrees, and the angle selected can change the amount of displacement of sled 185. For example, a lower angle of approximately 20 degrees for elongated slot 192 produces a minimum displacement of sled 185, and conversely, a greater angle of approximately 60 degrees produces a maximum displacement of sled 185. According to other aspects, elongated slot 192 can be replaced by a curved slot 196, which can further increase or decrease the amount of displacement of sled 185 depending on the direction of curvature of curved slot 196.

Referring to FIG. 20 and again to FIGS. 1-5 and 17-18, with the housing 12' again substantially removed for clarity, a mechanism assembly 198 is modified from mechanism assembly 170 and can be biased prior to or upon receipt of the test strip 18, and can apply a displacement force or a biasing force to either eject the test strip 18, or to retract a sled 200 after an ejection operation. The sled 200 is slidably and connectably engaged with respect to opposed and parallel oriented first and second guide rails 38, 40 as previously described herein, which are not shown in FIG. 20 for clarity. In the aspect shown in FIG. 20, mechanism assembly 198 includes biasing member 162 acting as a tension spring that is biased/extended during ejection of the test strip 18, thereby creating a biasing force acting in the loading direction "A". The biasing member 162 can be directly or indirectly connected to sled 200. Sled 200 in turn is rotatably connected to a first end 201 of a member such as an actuator arm 202 which is a beam structure having longitudinal rigidity to retain a longitudinal shape during operation under both the biasing load of biasing member 162 and a load manually applied by a user. A first pin 203 fixedly connected to first end 201 of actuator arm 202 is rotatably connected, either directly to sled 200, or to a structure 204 extending from sled 200. A second end 205 of actuator arm 202 is rotatably mounted to structure of housing 12' or to printed circuit board 24 using a mounting pin 206 which is fixed in position. A gear 208 is fixed to actuator arm 202 and also rotatably mounted to mounting pin 206 and includes multiple gear teeth 210. The gear teeth 210 are meshed with teeth of a rack gear set 212 extending into housing 12' from an ejection button 214. Ejection button 214 is slidably displaceable from the normal or test position shown in the sliding direction "T" by manual displacement by a user.

The use of mounting pin 206 and gear 208 provides for an opposite direction of displacement of ejection button 214 to eject test strip 18 compared to mechanism assembly 160, and similar to mechanism assembly 170. When ejection of test strip 18 is desired, the user manually displaces ejection button 214 in the sliding direction "T" which is parallel to but oppositely directed with respect to ejection direction "B". Similar to mechanism assemblies 160, 170 the velocity imparted to ejection button 214 by the user determines the velocity of discharge of test strip 18. As ejection button 214 is displaced in the sliding direction "T", the teeth of rack gear set 212 meshing with gear teeth 210 rotate actuator arm 202 (in a clockwise direction as viewed in FIG. 20), transferring a force applied through first pin 203 to displace sled 200 in the ejection direction "B". This rotation of actuator arm 202 displaces test strip 18 and simultaneously extends biasing member 162, creating a return biasing force in biasing member 162. When the user releases ejection button 214, the biasing force of extended biasing member 162 retracts sled 200, oppositely rotates actuator arm 202 (in a counter-clockwise direction as viewed in FIG. 20), and returns ejection button 214 parallel to the ejection direction "B" to the initial or test position shown, awaiting manual insertion of a next test strip. It is noted that the diameter of gear 208 and number of teeth 210, as well as the length of actuator arm 202 can increase or decrease the amount of displacement of sled 200.

Figure 21:
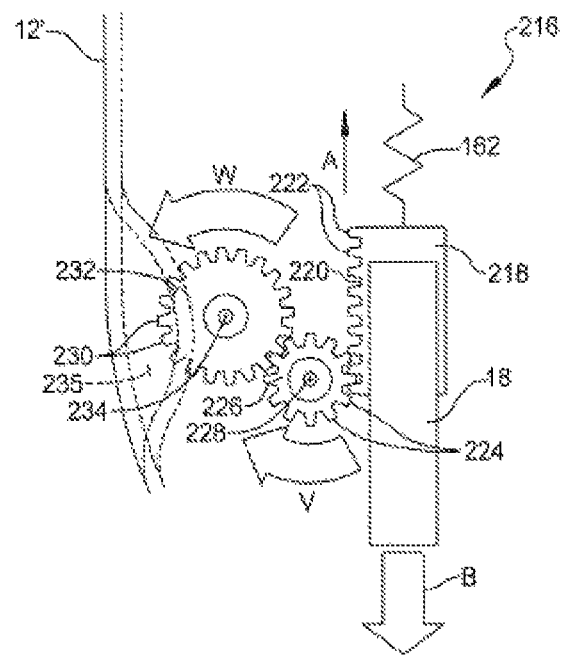
FIG. 21 shows a top plan view of another aspect for a multiple gear test strip ejection mechanism.

Referring to FIG. 21 and again to FIGS. 1-5 and 20, with the housing 12' again substantially removed for clarity, a mechanism assembly 216 is modified from mechanism assembly 198 and can be biased prior to or upon receipt of the test strip 18, and can apply a displacement force or a biasing force to either eject the test strip 18, or to retract a sled 218 after an ejection operation. The sled 218 is slidably and connectably engaged with respect to opposed and parallel oriented first and second guide rails 38, 40 as previously described herein, which are not shown in FIG. 21 for clarity. In the aspect shown in FIG. 21, mechanism assembly 216 includes biasing member 162 acting as a tension spring that is biased/extended during ejection of the test strip 18, thereby creating a biasing force acting in the loading direction "A". The biasing member 162 can be directly or indirectly connected to sled 218. Sled 218 includes a plurality of teeth 220 of a rack gear set 222 that mesh with teeth 224 of a first gear 226. First gear 226 is rotatably connected to housing 12' or to printed circuit board 24 using a first mounting pin 228. Teeth 224 mesh with teeth 230 of a second gear 232, which is rotatably connected to housing 12' or to printed circuit board 24 using a second mounting pin 234. According to several aspects, a portion of teeth 230 extend outwardly of housing 12' to be manually rotated by a user. According to other aspects, a portion of teeth 230 are accessible by a user via a cavity 235 created in housing 12' to provide access to teeth 230. First gear 226 rotates in a first direction "V" (counter-clockwise as viewed in FIG. 21) by manual rotation of second gear 232 in a second direction "W" (clockwise as viewed in FIG. 21) opposite to first direction "V". Rotation of first gear 226 meshes the teeth 220 of rack gear set 222, thereby displacing sled 218 and test strip 18 in the ejection direction "B". Release of second gear 232 by the user permits the biasing force of biasing member 162 to return mechanism assembly 216 to its normal, test position to manually receive a next test strip 18.

Figure 22:
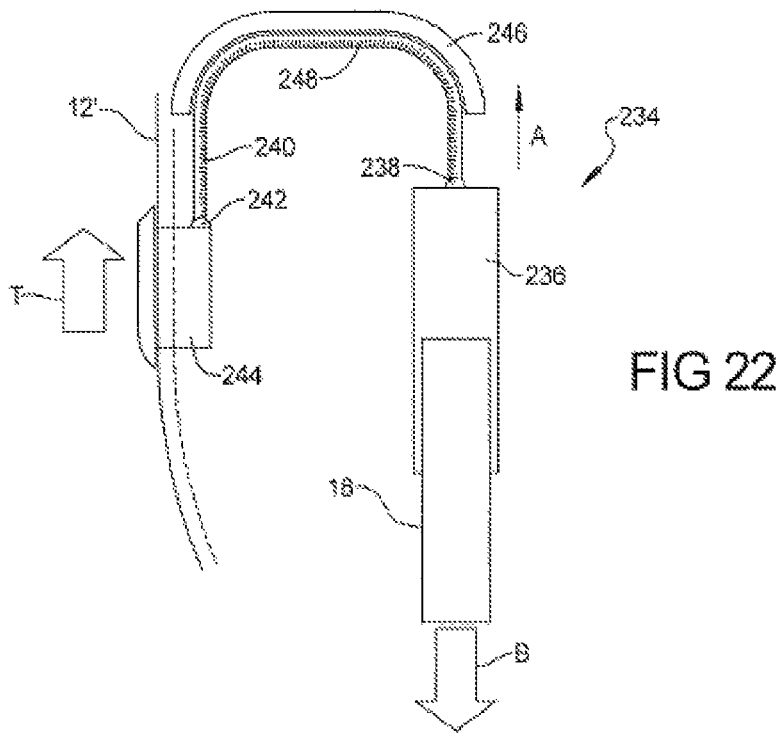
FIG. 22 shows a top plan view of another aspect for a flexible track actuated test strip ejection mechanism.

Referring to FIG. 22 and again to FIGS. 1-5 and 20, with the housing 12' again substantially removed for clarity, a mechanism assembly 234 includes a sled 236 operable to receive and/or eject a test strip 18. Sled 236 is connected to a first connecting end 238 of a flexible rail member 240. A second connecting end 242 of flexible rail member 240 is connected to an ejection button 244 which slidably operates similar to ejection button 166. Sled 236 is shown in the normal or test position having the test strip 18 manually loaded in the loading direction "A". To eject test strip 18, ejection button 244 is displaced in the sliding direction "T" which is opposite to ejection direction "B". The flexible rail member 240 is slidably retained by the contour of a guide member 246 fixed in housing 12'. The displacement of ejection button 244 displaces the entire length of flexible rail member 240 such that sled 236 is displaced by the same distance as ejection button 244 is displaced. A velocity or force applied to flexible rail member 240 directly affects the velocity of displacement of test strip 18.

Referring to FIG. 23 and again to FIGS. 1-5 and 22, with the housing 12' again substantially removed for clarity, a mechanism assembly 250 is modified from mechanism assembly 234 to omit sled 236. Mechanism assembly 250 includes a flexible rail member 252 similar to flexible rail member 240, but having a piston 254 defining a free end thereof. Flexible rail member 252 is slidably received in a rail housing 256 with piston 254 positioned to be able to directly contact test strip 18. An operating end 258 of flexible rail member 252 is acted on by a manual operator such as ejection button 166 previously described herein (not shown in this view for clarity) operable to displace flexible rail member 252 in a displacement direction "X". One or more clamps 260 can be used to orient rail housing 256 to align piston 254 with test strip 18 such that displacement of flexible rail member 252 causes ejection of test strip 18 in the ejection direction "B". Similar to previously described mechanism assemblies of the present disclosure, a velocity or force applied to flexible rail member 252 directly affects the velocity of displacement of test strip 18.

Referring to FIGS. 24A and 24B and again to FIGS. 1-5 and 23, with the housing 12' again substantially removed for clarity, a mechanism assembly 262 is modified from mechanism assembly 250 to add a second piston 263 at an opposite end of flexible rail member 252' with respect to piston 254 (not shown for clarity). Mechanism assembly 262 includes flexible rail member 252' having second piston 263 slidably disposed in a hollow bore 264 of a rail housing 266. Rail housing 256 is integrally connected to a bladder assembly 268 which when expanded draws a fluid 270 such as air into a chamber of bladder assembly 268. When compressed for example in a compression direction "Z" bladder assembly 268 displaces fluid 270 from within the chamber of bladder assembly 268 into hollow bore 264. With second piston 263 forming a sliding seal within hollow bore 264, fluid 270 displaces second piston 263 and therefore flexible rail member 252' in a displacement direction "AA" which acts to displace test strip 18 as described in reference to FIG. 23. Similar to previously described mechanism assemblies of the present disclosure, a velocity or force applied by fluid 270 on second piston 263 of flexible rail member 252' directly affects the velocity of displacement of test strip 18. According to other aspects, fluid 270 can be a hydraulic fluid, or substantially any fluid able to displace second piston 263 by compressing bladder assembly 268.

Figure 25A:
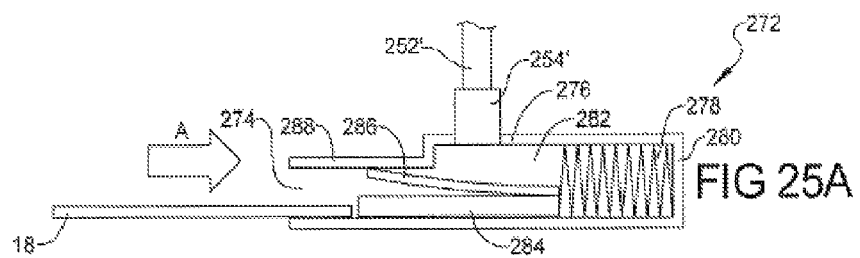
FIGS. 25A, 25B, 25C, 25D show front elevational views of another aspect for a stored energy actuated test strip ejection mechanism.
Figure 25B:
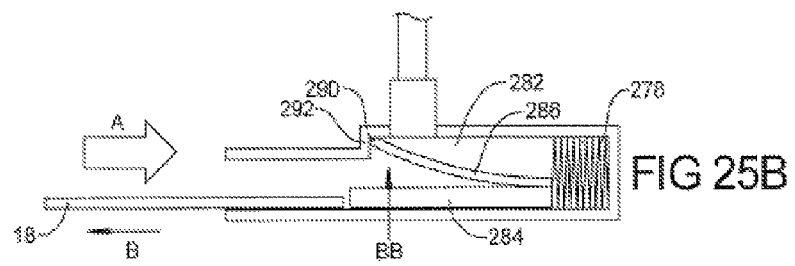

Referring to FIGS. 25A-25D and again to FIGS. 1-5 and FIG. 23, with the housing 12' again substantially removed for clarity, a mechanism assembly 272 operates using the stored energy of multiple biasing members to eject a test strip 18. Mechanism assembly 272 receives test strip 18 in the loading direction "A" into a first opening or cavity 274 that communicates with a housing 276. A first biasing member 278 such as a compression spring is positioned in contact with an end wall 280 of housing 276 in a second opening or cavity 282, which is larger than first cavity 274. As shown in FIGS. 25A and 25B, the test strip 18 when inserted contacts a sled 284 slidably disposed in second cavity 282, which contacts an end of first biasing member 278 facing away from end wall 280 and compresses first biasing member 278. As shown in FIG. 25A, a second biasing member 286 such as a leaf or plate spring may be connected to sled 284 and initially extends freely into the first cavity 274 and is in sliding contact with an upper wall 288 of first cavity 274. As the sled 284 is displaced in the loading direction "A" by test strip 18, a free end 290 of second biasing member 286 is displaced into second cavity 282 where the biasing force of second biasing member 286 displaces free end 290 in a direction "BB" away from sled 284 and into contact with a second end wall 292 of second cavity 282, where a stiffness of second biasing member 286 restrained against second end wall 292 prevents first biasing member 278 from acting to eject test strip 18.

Figure 25C:
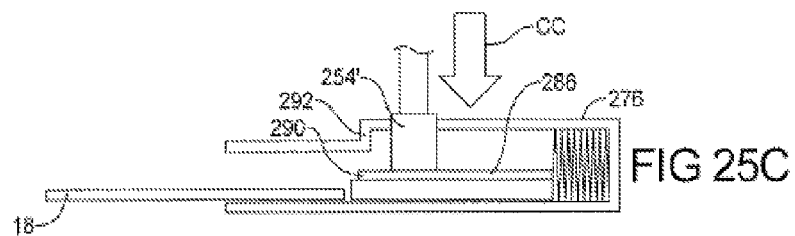
Figure 25D:
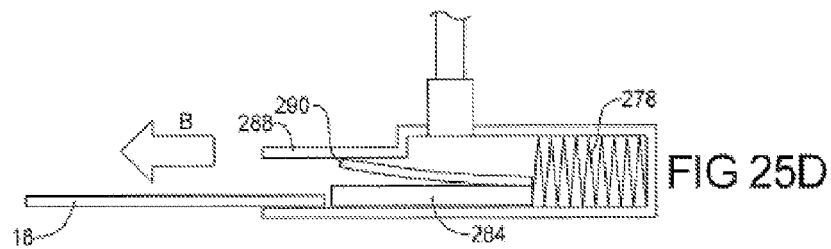

As shown in FIGS. 25B-25D, the piston 254' of flexible rail member 252' is slidably received in an aperture of housing 276 directly in alignment with second biasing member 286. To eject test strip 18, a force acting on flexible rail member 252' displaces piston 254' in a displacement direction "CC" into second cavity 282 and into direct contact with second biasing member 286, thereby forcing free end 290 away from contact with second end wall 292. This permits the biasing force of compressed first biasing member 278 to displace sled 284 and free end 290 into the first cavity 274. The biasing force of first biasing member 278 overcomes the frictional contact between piston 254' and second biasing member 286 such that sled 284 is displaced in the ejection direction "B" to eject test strip 18. Release of the force acting on flexible rail member 252' and piston 254' permits biased retraction of piston 254' back to the original position shown in FIG. 25A. Only a single ejection speed of test strip 18 is provided by mechanism assembly 272, which is predetermined by the biasing force, length, spring constant, and the like of the first and second biasing members 278, 286.

Referring to FIG. 26 and again to FIGS. 1-5, with the housing 12' again substantially removed for clarity, a mechanism assembly 294 operates using a frictional contact ejection roller to eject a test strip 18. Mechanism assembly 294 receives test strip 18 in the loading direction "A" into a U-shaped trough 296 having opposed first and second side walls 298, 300, and a joining wall 302 oriented substantially perpendicular to first and second side walls 298, 300. A frictional roller 304 is rotatably supported by first and second side walls 298, 300 using a pin 306 extending through both first and second side walls 298, 300 and frictional roller 304 allowing frictional roller to rotate with respect to an axis of rotation 308. As test strip 18 is inserted friction contact with frictional roller 304 occurs, such that test strip 18 is in continuous contact with frictional roller 304 at all times during installation, testing and until ejection. To eject test strip 18, the user can manually rotate frictional roller 304 in a rotational direction "DD", which ejects test strip 18 in the ejection direction "B". Optionally, an electric motor 310 can be provided in housing 12', which is connected to rotate friction roller 304 when energized. In these aspects, the user can operate motor 310 until test strip 18 is visibly ejected from housing 12'.

Figure 27:
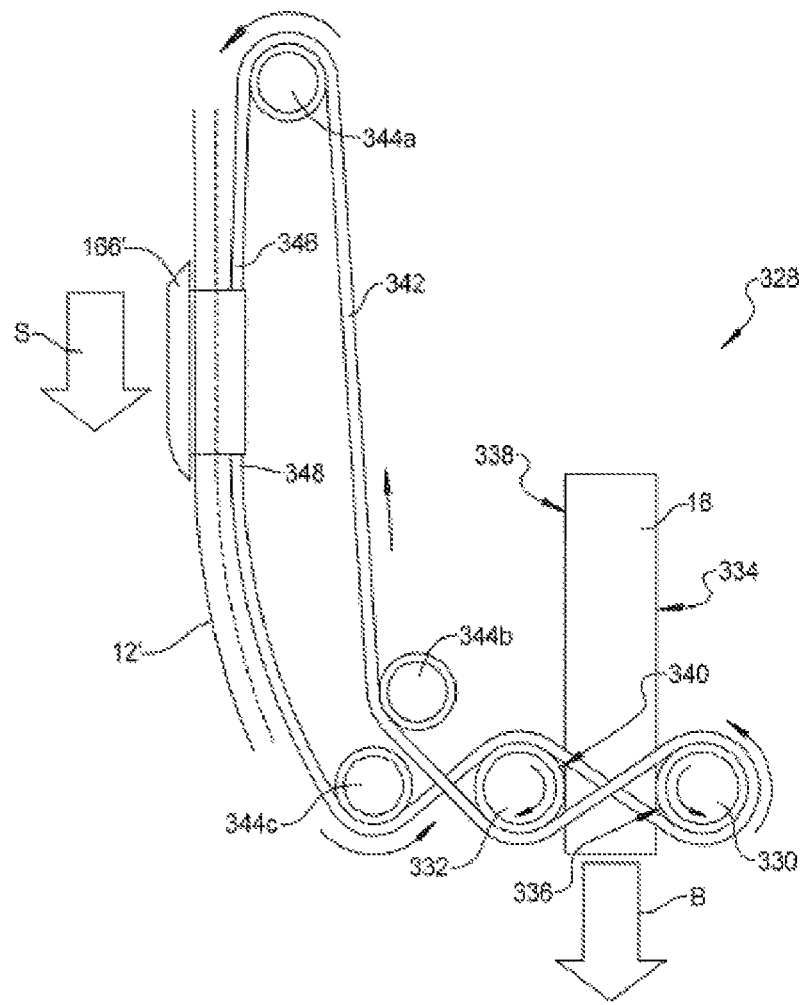
FIG. 27 shows a top plan view of another aspect for a combination racetrack/roller test strip ejection mechanism.

Referring to FIG. 27 and again to FIGS. 1-5, with the housing 12' again substantially removed for clarity, a mechanism assembly 328 operates using a flexible band and a set of rollers to eject a test strip 18. With test strip 18 in the test position shown, test strip 18 can be ejected as follows. Opposed and spatially separated first and second rollers 330, 332 rotatably connected to housing 12' or to printed circuit board 24 individually contact the test strip 18 using an outer surface 336 of first roller 330 in frictional contact with a first edge 334 of test strip 18, and an outer surface 340 of second roller 332 in frictional contact with a second edge 338 of test strip 18. A flexible band 342 engages the first and second rollers 330, 332 and is guided by a plurality of guide rollers 344a, 344b, 344c rotatably connected to housing 12' or to printed circuit board 24. Opposed ends 346, 348 of flexible band 342 are connected to opposite ends of ejection button 166'. When ejection button 166' is manually displaced in the sliding direction "S" by the user, the flexible band 342 causes oppositely directed rotation of the first and second rollers 330, 332 because of the directionally crossed portions of flexible band 342 proximate to first and second rollers 330, 332. In the example shown, first roller 330 rotates counterclockwise, while second roller 332 rotates clockwise. The frictional contact of the first and second rollers 330, 332 with the first and second outer edges 334, 338 of test strip 18 eject test strip 18 in the ejection direction "B".

Referring to FIGS. 28A-28B and again to FIGS. 1-5, with the housing 12' again substantially removed for clarity, a mechanism assembly 400 operates using the energy produced by an electric motor such as a piezo-electric linear micro motor to eject a test strip 18. According to several embodiments, mechanism assembly 400 initially manually receives test strip 18 in the loading direction "A" which contacts an armature 402 or piston positioned in an armature cavity 404 of a piezo-electric linear micro motor 406, available for example from New Scale Technologies, Inc. of Victor, N.Y. A positive potential voltage 408 and a negative potential voltage 410 of a power supply 412 such as a battery are connected to motor 406 using a switch 414 to cause rotation/displacement of armature 402 in a direction of displacement "EE". When test strip manual loading in loading direction "A" is used to inwardly displace the armature 402, switch 414 is initially positioned in an open position. Rotation/displacement of armature 402 displaces test strip 18 in the ejection direction "B" thereby ejecting test strip 18. According to several embodiments, when switch 414 is released, motor 406 is de-energized, and the armature 402 is retracted into a test strip receiving slot 416 by a magnetic force of a magnet 418 connected to motor 406. Magnet 418 is positioned proximate to the armature cavity 404 and acts to magnetically retract the armature 402 into the armature cavity 404 when the motor is de-energized where the armature 402 is directly contacted by a next or subsequently inserted test strip 18. For embodiments not including magnet 418, the armature 402 will remain extended within the test strip receiving slot 416 until a subsequent test strip 18 is inserted, which will act using the force applied to the test strip 18 by the user to manually displace armature 402 into the armature cavity 404 to a test strip test position. According to further embodiments, motor 406 can be operated in each of the ejection direction "B" and the loading direction "A". This allows powered full retraction of the armature 402 to the test strip test position for testing and prior to operation of motor 406 for ejection. Operation in both directions will, however, consume additional power from power supply 412.

Referring to FIG. 29 and again to FIGS. 28A-28B, according to further aspects, an analysis device 420 includes a housing 422 that provides an electrically operated or a motorized mechanism assembly such as mechanism assembly 400. Housing 422 can provide a digital display/user interface 424 in the form of a touchscreen or a set of flexible membrane actuation buttons, providing multiple digital readout screens, including a digital test readout screen 426 which visually displays a digital test result such as a blood glucose level and a units indicator 428. According to several embodiments, an ejection function provided by display/user interface 424 can include a digital eject button 430 provided during operation of the digital test readout screen 426 that prompts the user to eject the test strip 18 after the test is complete. Physical contact by the user with digital eject button 430 initiates automatic ejection of test strip 18 as described in reference to FIG. 28B. Advantages of the use of digital display/user interface 424 include elimination of a mechanical button required for test strip ejection, elimination of the aperture required through the analysis device housing for the mechanical button which reduces the openings in the analysis device housing to only the test strip receiving slot thereby mitigating fluid or debris ingress, the capability to select between different language readouts, adjustment of test strip ejection force (described in reference to FIG. 30), and elimination of random variance between test strip ejection speeds/distances. Digital display/user interface 424 also provides for ejection of the test strip if a test "error" occurs when no test result is available, requiring the test strip to be ejected and replaced.

Referring to FIG. 30 and again to FIG. 29, analysis device 420 can also provide multiple other screen displays on display/user interface 424 by sequential user contact of a function bar 432. In the example shown, the user can manually select an amount of ejection force created by the mechanism assembly to eject the test strip. For this function, the user actuates function bar 432 to select a set force screen 434, which provides a digital force increase button 436 and a digital force decrease button 438. By selecting/contacting either force increase button 436 or force decrease button 438, a repeatable increase or decrease in test strip ejection force is made and saved using a save button 437 in a memory of analysis device 420. For example, the user can select a minimum ejection force which substantially allows the test strip 18 to fall away from analysis device 420 if positioned directly over a waste container, or the user can increase the ejection force and therefore the ejection velocity which will eject the test strip 18 for a horizontal distance required to reach the waste container. The force increase button 436 or the force decrease button 438 can be quickly pressed and released to make an incremental change in operating force, or held to make larger changes in operating force. A cancel button 439 can be selected to cancel any saved force values.

Referring to FIG. 31 and again to FIG. 29, while still acting in digital test readout screen 426, after the user contacts digital eject button 430 to initiate test strip ejection, an ejection actuation arrow sequence 440 can replace digital eject button 430. Ejection actuation arrow sequence 440 provides visual indication to the user of test strip 18 ejection actuation as well as the ejection direction "B". In this operating mode, variation of a swipe speed (velocity) of the user's hand or finger over the actuation arrow sequence 440 directly varies the test strip ejection speed.

Figure 32:
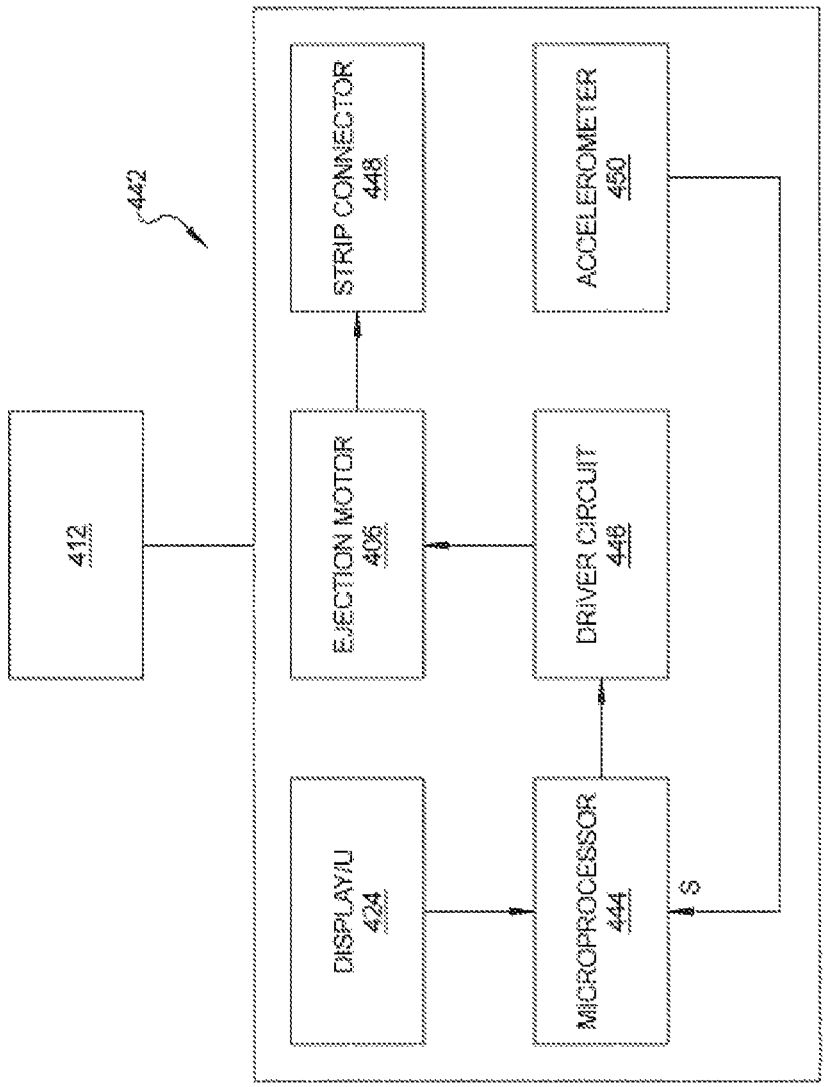
FIG. 32 shows a diagram of a motor operated medical analysis device test strip ejector system.

Referring to FIG. 32 and again to FIGS. 28A, 28B and 29-31, an operating system 442 for analysis device 420 is powered by power supply 412 which can be rechargeable or non-rechargeable. Operating system 442 includes display/user interface 424 connected to a microprocessor 444 used for example to control direction of operation and operating speed of motor 406. A driver circuit 446 connects the microprocessor 444 to motor 406 which is connected to and displaces a strip connector 448. According to further embodiments, operating system 442 can include an accelerometer 450 whose output is a signal "S" input to microprocessor 444. Accelerometer 450 can be used in lieu of eject button 430 and operates as follows. Accelerometer 450 becomes active only after the test phase is complete or when a test error occurs and the test strip is to be ejected. Once accelerometer 450 is activated, the user orients analysis device 420 over a waste container in a vertical orientation which is sensed by the accelerometer 450, creating signal "S" sent to the microprocessor 444 and used by microprocessor 444 to initiate automatic test strip ejection. If analysis device 420 is held in the vertical orientation during test result viewing, a vertical to horizontal and return to vertical orientation change to analysis device 420 will act to create signal "S" causing ejection of the test strip 18. In addition, the above noted orientation change can also include a deliberate manual shake or "shaking motion" of analysis device 420 in any orientation that is sensed by accelerometer 450, which can also be used to initiate test strip ejection.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A test strip ejector system for receiving and ejecting a test strip of a fluid testing medical device, the system comprising:
a mechanism assembly supported by the fluid testing medical device whereby user actuation of the mechanism assembly induces displacement of the test strip in at least a test strip ejection direction to eject the test strip, the mechanism assembly including:
a power source; and
an electric motor connected to the power source, the electric motor having an armature displaced when the electric motor is energized; and
a digital display/user interface, selection of an ejection function presented on the digital display/user interface acting to initiate operation of the electric motor and displacement of the armature thereby displacing the test strip in the ejection direction.

2. The test strip ejector system for receiving and ejecting a test strip of a fluid testing medical device of claim 1, wherein the test strip is positioned in direct contact with the armature in a test strip test position.

3. The test strip ejector system for receiving and ejecting a test strip of a fluid testing medical device of claim 2, further including a motor housing having the motor positioned therein and an armature cavity, wherein the armature is initially positioned in an extended position such that manual displacement of the test strip in a loading direction acts to inwardly displace the armature to the test strip test position.

4. The test strip ejector system for receiving and ejecting a test strip of a fluid testing medical device of claim 3, wherein the mechanism assembly further includes a magnet positioned proximate to the armature cavity acting to magnetically retract the armature into the armature cavity when the motor is de-energized.

5. The test strip ejector system for receiving and ejecting a test strip of a fluid testing medical device of claim 2, further including a motor housing having the motor positioned therein and an armature cavity, wherein the armature is initially positioned in a retracted position within the armature cavity such that manual displacement of the test strip in a loading direction acts to position the test strip in direct contact with the armature defining the test strip test position.

6. The test strip ejector system for receiving and ejecting a test strip of a fluid testing medical device of claim 1, further including an operating system including a microprocessor connected to the display/user interface, the microprocessor acting to control direction of operation and operating speed of the motor.

7. The test strip ejector system for receiving and ejecting a test strip of a fluid testing medical device of claim 6, wherein the operating system further includes an accelerometer having an output connected to the microprocessor.

8. The test strip ejector system for receiving and ejecting a test strip of a fluid testing medical device of claim 7, wherein the accelerometer is active only after the test phase is complete or when a test error occurs and the test strip is to be ejected, when the accelerometer is active a vertical orientation of the analysis device is sensed by the accelerometer creating an accelerometer signal acting to initiate ejection of the test strip.

9. The test strip ejector system for receiving and ejecting a test strip of a fluid testing medical device of claim 7, wherein the accelerometer is active only after the test phase is complete or when a test error occurs and the test strip is to be ejected, thereafter if the analysis device is held in a vertical orientation during test result viewing, a vertical to horizontal and return to vertical orientation change to the analysis device is sensed by the accelerometer and a signal generated by the accelerometer acts to initiate ejection of the test strip.

10. The test strip ejector system for receiving and ejecting a test strip of a fluid testing medical device of claim 7, wherein a deliberate shaking motion of the analysis device after the test phase is complete is sensed by the accelerometer creating a signal generated by the accelerometer acting to initiate ejection of the test strip.

11. The test strip ejector system for receiving and ejecting a test strip of a fluid testing medical device of claim 6, wherein the operating system further includes a driver circuit connecting the microprocessor to the motor.

12. The test strip ejector system for receiving and ejecting a test strip of a fluid testing medical device of claim 1, further including a digital ejection button presented on the digital display/user interface, selection of the ejection button acting to initiate operation of the electric motor and displacement of the armature thereby displacing the test strip in the ejection direction.

13. The test strip ejector system for receiving and ejecting a test strip of a fluid testing medical device of claim 12, wherein displacement of the ejection button in a sliding direction acts to displace the test strip in the ejection direction.

14. The test strip ejector system for receiving and ejecting a test strip of a fluid testing medical device of claim 12, wherein a velocity of displacement of the ejection button is directly related to a velocity of ejection of the test strip.

15. The test strip ejector system for receiving and ejecting a test strip of a fluid testing medical device of claim 12, further including a reverse operation of the motor, wherein when the ejection button is released reverse operation of the motor inwardly retracts the armature into a housing of the fluid testing medical device.

16. The test strip ejector system for receiving and ejecting a test strip of a fluid testing medical device of claim 1, wherein the motor is a piezo-electric linear micro motor operating when energized to both rotate and axially displace the armature.

17. The test strip ejector system for receiving and ejecting a test strip of a fluid testing medical device of claim 1, wherein the motor is oppositely operable in each of the ejection direction and a test strip loading direction allowing powered full retraction of the armature to the test strip test position and prior to operation of the motor for test strip ejection.

18. The test strip ejector system for receiving and ejecting a test strip of a fluid testing medical device of claim 1, wherein the digital display/user interface provides for a plurality of user selected operating screens, wherein a force increase and a force decrease button are provided on a selected one of the operating screens, selection of one of the force increase or force decrease buttons acting to increase or decrease a force applied by the motor to increase or decrease a velocity of the test strip during ejection.

19. A test strip ejector system for receiving and ejecting a test strip of a fluid testing medical device, the system comprising:
a mechanism assembly supported by the fluid testing medical device whereby user actuation of the mechanism assembly induces displacement of the test strip in at least a test strip ejection direction to eject the test strip, the mechanism assembly including:
a power source; and
an electric motor connected to the power source, the electric motor having an armature displaced when the electric motor is energized;
a digital display/user interface, selection of an ejection function presented on the digital display/user interface acting to initiate operation of the electric motor and displacement of the armature thereby displacing the test strip in the ejection direction; and
an operating system including a microprocessor connected to the display/user interface, the microprocessor acting to control direction of operation and operating speed of the motor.

20. The test strip ejector system for receiving and ejecting a test strip of a fluid testing medical device of claim 19, further including a digital ejection button presented on the digital display/user interface, selection of the ejection button acting to initiate operation of the electric motor and displacement of the armature thereby displacing the test strip in the ejection direction.

21. The test strip ejector system for receiving and ejecting a test strip of a fluid testing medical device of claim 20, wherein the ejection button is displaceable in a sliding direction which is parallel with the ejection direction to initiate test strip ejection.

22. The test strip ejector system for receiving and ejecting a test strip of a fluid testing medical device of claim 21, wherein a velocity imparted to the ejection button by a user directly determines a discharge velocity of the test strip.

23. The test strip ejector system for receiving and ejecting a test strip of a fluid testing medical device of claim 19, wherein the operating system further includes an accelerometer having an output connected to the microprocessor, the accelerometer acting to automatically initiate ejection of the test strip by a change in orientation of the fluid testing medical device.

24. The test strip ejector system for receiving and ejecting a test strip of a fluid testing medical device of claim 19, further including a switch connected between the power source and the motor, the switch actuated by selection of the ejection function.

25. The test strip ejector system for receiving and ejecting a test strip of a fluid testing medical device of claim 19, wherein the display/user interface includes set force screen having a save button acting when selected to save a selected motor operating force in a memory of the analysis device.

26. The test strip ejector system for receiving and ejecting a test strip of a fluid testing medical device of claim 19, wherein the mechanism assembly is normally positioned in a test strip test position having the armature retracted in a motor housing containing the motor.

27. The test strip ejector system for receiving and ejecting a test strip of a fluid testing medical device of claim 19, wherein the test strip is manually loaded in a loading direction in a loading operation and the loading operation does not displace any members of the mechanism assembly.

28. The test strip ejector system for receiving and ejecting a test strip of a fluid testing medical device of claim 19, wherein the ejection button is slidably displaced on the digital display/user interface in a sliding direction to directly eject the test strip.

29. A test strip ejector system for receiving and ejecting a test strip of a fluid testing medical device, the system comprising:
  a mechanism assembly supported by the fluid testing medical device whereby user actuation of the mechanism assembly induces displacement of a test strip slidably received in the fluid testing medical device in at least a test strip ejection direction to eject the test strip, the mechanism assembly including:
    a power source; and
    an electric motor connected to the power source, the electric motor acting to displace a piston which is in contact with the test strip when the electric motor is energized;
  an operating system including:
    a microprocessor connected to the power source and the motor, the microprocessor acting to control direction of operation and operating speed of the motor; and
    an accelerometer acting when an orientation of the fluid testing medical device is changed to initiate operation of the motor.

30. The test strip ejector system for receiving and ejecting a test strip of a fluid testing medical device of claim 29, further including a digital display/user interface providing a test result readout.

31. The test strip ejector system for receiving and ejecting a test strip of a fluid testing medical device of claim 30, wherein the digital display/user interface provides for a plurality of user selected operating screens, wherein a force increase and a force decrease button are provided on a selected one of the operating screens, selection of one of the force increase or force decrease buttons acting to increase or decrease a force applied by the motor to increase or decrease a velocity of the test strip during ejection.

32. The test strip ejector system for receiving and ejecting a test strip of a fluid testing medical device of claim 30, further including a switch connected between the power source and the motor, the switch actuated by selection of the ejection function visibly presented on the digital display/user interface.

33. A test strip ejector system for receiving and ejecting a test strip of a fluid testing medical device, the system comprising:
  a test strip slidably received in a receiving slot of the fluid testing medical device in a test strip loading direction;
  a mechanism assembly supported by the fluid testing medical device whereby user actuation of the mechanism assembly induces displacement of the test strip in a test strip ejection direction opposite to the loading direction to eject the test strip, the mechanism assembly including:
    a power source; and
    an electric motor connected to the power source, the electric motor having an armature displaced when the electric motor is energized; and
  a digital display/user interface, selection of an ejection function presented on the digital display/user interface acting to initiate operation of the electric motor and displacement of the armature thereby displacing the test strip in the ejection direction.

34. The test strip ejector system for receiving and ejecting a test strip of a fluid testing medical device of claim 33, wherein the digital display/user interface includes an eject test strip button acting when manually selected to initiate operation of the electric motor.

35. The test strip ejector system for receiving and ejecting a test strip of a fluid testing medical device of claim 33, wherein an ejection force acting to eject the test strip is selected by the user using a set force button provided on the digital display/user interface.

36. A glucose test meter having a test strip ejector system for receiving and ejecting a test strip, the test meter comprising:
  a meter body having a receiving slot;
  a test strip slidably received in the receiving slot of the meter body in a test strip loading direction; and
  a mechanism assembly supported by the meter body whereby user actuation of the mechanism assembly induces displacement of the test strip in a test strip ejection direction opposite to the loading direction to eject the test strip, the mechanism assembly including:
    a power source; and
    an electric motor connected to the power source, the electric motor having an armature displaced when the electric motor is energized.

37. The glucose test meter having a test strip ejector system for receiving and ejecting a test strip of claim 36, a digital display/user interface, selection of an ejection function presented on the digital display/user interface acting to initiate operation of the electric motor and displacement of the armature thereby displacing the test strip in the ejection direction.

38. The glucose test meter having a test strip ejector system for receiving and ejecting a test strip of claim 36, wherein the test strip is manually inserted to a test position defining direct contact between the test strip and the armature, and maintained in direct contact with the armature during motion in the ejection direction.

39. A method for receiving and ejecting a test strip by a mechanism assembly of a fluid testing medical device, the mechanism assembly including a power source, an electric motor having an armature, a digital display/user interface and an operating system, the method comprising:
  supporting the mechanism assembly by the fluid testing medical device;

connecting the electric motor to the power source;
manually inserting a test strip into the fluid testing medical device; and
selecting an ejection function presented on the digital display/user interface to initiate operation of the electric motor and displacement of the armature thereby displacing the test strip in an ejection direction.

40. The method of claim 39, further including connecting a microprocessor of the operating system to the display/user interface and to the electric motor.

41. The method of claim 40, further including automatically controlling a direction of operation and operating speed of the motor using the microprocessor.

42. The method of claim 39, further including manually selecting an ejection button presented on the digital display/user interface during the selecting operation.

43. The method of claim 42, further including manually sliding the ejection button across the digital display/user interface during the selecting operation to increase an ejection speed of the test strip.

\* \* \* \* \*